US006726685B2

(12) United States Patent
To et al.

(10) Patent No.: US 6,726,685 B2
(45) Date of Patent: Apr. 27, 2004

(54) INTERVERTEBRAL DISC DEVICE EMPLOYING LOOPED PROBE

(75) Inventors: Kevin To, Campbell, CA (US); Le T. Le, San Jose, CA (US); Andy Uchida, Mountain View, CA (US); Hugh Sharkey, Menlo Park, CA (US); John Ashley, San Francisco, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/876,833

(22) Filed: Jun. 6, 2001

(65) Prior Publication Data

US 2002/0188284 A1 Dec. 12, 2002

(51) Int. Cl.$^7$ ................................ H61B 18/18
(52) U.S. Cl. ...................... 606/50; 606/14; 606/33
(58) Field of Search .................. 606/41, 14, 27, 606/33, 49, 50

(56) References Cited

U.S. PATENT DOCUMENTS

| | | |
|---|---|---|
| 2,090,923 A | 8/1937 | Wappler |
| 3,178,728 A | 4/1965 | Christensen |
| 3,579,643 A | 5/1971 | Morgan |
| 3,776,230 A | 12/1973 | Neefe |
| 3,856,015 A | 12/1974 | Iglesias |
| 3,867,728 A | 2/1975 | Substad et al. |
| 3,879,767 A | 4/1975 | Substad |
| 3,886,600 A | 6/1975 | Kahn et al. |
| 3,938,198 A | 2/1976 | Kahn et al. |
| 3,945,375 A | 3/1976 | Banko |
| 3,987,499 A | 10/1976 | Scharbach et al. |
| 3,992,725 A | 11/1976 | Homsy |
| 4,043,342 A | 8/1977 | Morrison, Jr. |
| 4,074,718 A | 2/1978 | Morrison, Jr. |
| 4,085,466 A | 4/1978 | Goodfellow et al. |
| 4,129,470 A | 12/1978 | Homsy |
| 4,134,406 A | 1/1979 | Iglesias |
| 4,224,696 A | 9/1980 | Murray et al. |
| 4,224,697 A | 9/1980 | Murray et al. |
| 4,326,529 A | 4/1982 | Doss et al. |
| 4,344,193 A | 8/1982 | Kenny |
| 4,362,160 A | 12/1982 | Hiltebrandt |
| 4,375,220 A | 3/1983 | Matvias |
| 4,381,007 A | 4/1983 | Doss |
| 4,397,314 A | 8/1983 | Vaguine |
| 4,476,862 A | 10/1984 | Pao |
| 4,483,338 A | 11/1984 | Bloom et al. |
| 4,517,965 A | 5/1985 | Ellison |
| 4,517,975 A | 5/1985 | Garito et al. |
| 4,590,934 A | 5/1986 | Malis et al. |
| 4,593,691 A | 6/1986 | Lindstrom et al. |
| 4,597,379 A | 7/1986 | Kihn et al. |
| 4,601,705 A | 7/1986 | McCoy |
| 4,651,734 A | 3/1987 | Doss et al. |
| 4,811,733 A | 3/1989 | Borsanyi et al. |
| 4,811,743 A | 3/1989 | Stevens |
| 4,815,462 A | 3/1989 | Clark |
| 4,838,859 A | 6/1989 | Strassmann |
| 4,846,175 A | 7/1989 | Frimberger |
| 4,873,976 A | 10/1989 | Schreiber |
| 4,894,063 A | 1/1990 | Nashef |
| 4,895,148 A | 1/1990 | Bays et al. |
| 4,907,585 A | 3/1990 | Schachar |
| 4,907,589 A | 3/1990 | Cosman |
| 4,924,865 A | 5/1990 | Bays et al. |
| 4,944,727 A | 7/1990 | McCoy |
| 4,950,234 A | 8/1990 | Fujioka et al. |
| 4,950,267 A | 8/1990 | Ishihara et al. |
| 4,955,882 A | 9/1990 | Hakky |
| 4,966,597 A | 10/1990 | Cosman |
| 4,976,709 A | 12/1990 | Sand |
| 4,976,715 A | 12/1990 | Bays et al. |
| 4,998,933 A | 3/1991 | Eggers et al. |
| 5,007,908 A | 4/1991 | Rydell |
| 5,009,656 A | 4/1991 | Reimels |
| 5,084,043 A | 1/1992 | Hertzmann et al. |
| 5,085,657 A | 2/1992 | Ben-Simhon |
| 5,085,659 A | 2/1992 | Rydell |
| 5,098,430 A | 3/1992 | Fleenor |
| 5,100,402 A | 3/1992 | Fan |
| 5,103,804 A | 4/1992 | Abele et al. |
| 5,114,402 A | 5/1992 | McCoy |
| 5,152,748 A | 10/1992 | Chastagner |

(List continued on next page.)

FOREIGN PATENT DOCUMENTS

| | | |
|---|---|---|
| CA | 2188668 | 11/1995 |
| EP | 0 257 116 | 3/1988 |
| EP | 0274705 A1 | 7/1988 |

(List continued on next page.)

OTHER PUBLICATIONS

Lee Beadling, "Bi–Polar electrosurgical devices: Scultping the future of arthroscopy," *Orthopedics today*, vol. 7, No. 1, Jan. 1997.

"What New in Office Electrosurgery? Radiosurgery!," *ellman International Manufacturing, Inc.*, pp. 1–15.

Martin H. Savitz, "Same–day microsurgical arthroscopic lateral–approach laser–assisted (SMALL) fluoroscopic discectomy," *J. Neurosurg* 80: 1039–1045, 1994.

(List continued on next page.)

*Primary Examiner*—Linda C. M. Dvorak
*Assistant Examiner*—Henry M Johnson
(74) *Attorney, Agent, or Firm*—Fish & Richardson P.C.

(57) ABSTRACT

An intervertebral disc device is provided comprising a probe capable of being extended from a distal end of an introducer that is percutaneously delivered into an interior of an intervertebral disc, the probe forming a loop when extended from the distal end of the introducer, the loop having first and second proximal ends external to the introducer which are brought together adjacent the introducer distal end to form the loop by the proximal ends being either attached to or entering the distal end of the introducer; and a proximal handle for externally causing the probe to be extended from the distal end of the introducer and externally guiding the probe within an intervertebral disc.

33 Claims, 28 Drawing Sheets

U.S. PATENT DOCUMENTS

| | | |
|---|---|---|
| 5,178,620 A | 1/1993 | Eggers et al. |
| 5,186,181 A | 2/1993 | Franconi et al. |
| 5,191,883 A | 3/1993 | Lennox et al. |
| 5,192,267 A | 3/1993 | Shapira et al. |
| 5,201,729 A | 4/1993 | Hertzmann et al. |
| 5,201,730 A | 4/1993 | Easley et al. |
| 5,201,731 A | 4/1993 | Hakky |
| 5,213,097 A | 5/1993 | Zeindler |
| 5,230,334 A | 7/1993 | Klopotek |
| 5,242,439 A | 9/1993 | Larsen et al. |
| 5,242,441 A | 9/1993 | Avitall |
| 5,261,906 A | 11/1993 | Pennino et al. |
| 5,267,994 A | 12/1993 | Gentelia et al. |
| 5,275,151 A | 1/1994 | Shockey et al. |
| 5,279,559 A | 1/1994 | Barr |
| 5,284,479 A | 2/1994 | de Jong |
| 5,304,169 A | 4/1994 | Sand |
| 5,308,311 A | 5/1994 | Eggers et al. |
| 5,311,858 A | 5/1994 | Adair |
| 5,320,115 A | 6/1994 | Kenna |
| 5,323,778 A | 6/1994 | Kandarpa et al. |
| 5,334,193 A | 8/1994 | Nardella |
| 5,342,357 A | 8/1994 | Nardella |
| 5,348,554 A | 9/1994 | Imran et al. |
| 5,352,868 A | 10/1994 | Denen et al. |
| 5,354,331 A | 10/1994 | Schachar |
| 5,364,395 A | 11/1994 | West, Jr. |
| 5,366,443 A | 11/1994 | Eggers et al. |
| 5,366,490 A | 11/1994 | Edwards et al. |
| 5,382,247 A | 1/1995 | Cimino et al. |
| 5,397,304 A | 3/1995 | Truckai |
| 5,401,272 A | 3/1995 | Perkins |
| 5,415,633 A | 5/1995 | Lazarus et al. |
| 5,423,806 A | 6/1995 | Dale et al. |
| 5,433,739 A | 7/1995 | Sluijter et al. |
| 5,437,661 A | 8/1995 | Rieser |
| 5,437,662 A | 8/1995 | Nardella |
| 5,451,223 A | 9/1995 | Ben-Simhon |
| 5,458,596 A | 10/1995 | Lax et al. |
| 5,464,023 A | 11/1995 | Viera |
| 5,465,737 A | 11/1995 | Schachar |
| 5,472,426 A | 12/1995 | Bonati et al. |
| 5,484,403 A | 1/1996 | Yoakum et al. |
| 5,484,432 A | 1/1996 | Sand |
| 5,484,435 A | 1/1996 | Fleenor et al. |
| 5,487,757 A | 1/1996 | Truckai et al. |
| 5,498,258 A | 3/1996 | Hakky et al. |
| 5,500,012 A | 3/1996 | Brucker et al. |
| 5,507,812 A | 4/1996 | Moore |
| 5,514,130 A | 5/1996 | Baker |
| 5,520,645 A | 5/1996 | Imran et al. |
| 5,524,338 A | 6/1996 | Martyniuk et al. |
| 5,527,331 A | 6/1996 | Kresch et al. |
| 5,542,920 A | 8/1996 | Cherif Cheikh |
| 5,569,242 A | 10/1996 | Lax et al. |
| 5,582,609 A | 12/1996 | Swanson et al. |
| 5,599,346 A | 2/1997 | Edwards et al. |
| 5,630,839 A | 5/1997 | Corbett, III et al. |
| 5,673,707 A | 10/1997 | Chandrasekaran |
| 5,681,282 A | 10/1997 | Eggers et al. |
| 5,683,366 A | 11/1997 | Eggers et al. |
| 5,688,270 A | 11/1997 | Yates et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,718,702 A | 2/1998 | Edwards |
| 5,785,705 A | 7/1998 | Baker |
| 5,807,306 A | 9/1998 | Shapland et al. |
| 5,810,802 A | 9/1998 | Panescu et al. |
| 5,810,809 A | 9/1998 | Rydell |
| 5,836,892 A | 11/1998 | Lorenzo |
| 5,836,947 A | 11/1998 | Fleischman et al. |
| 5,871,469 A | 2/1999 | Eggers et al. |
| 5,871,501 A | 2/1999 | Leschinsky et al. |
| 5,882,346 A | 3/1999 | Pomeranz et al. |
| 5,885,217 A | 3/1999 | Gisselberg et al. |
| 5,885,278 A | 3/1999 | Fleischman et al. |
| 5,910,129 A | 6/1999 | Koblish et al. |
| 5,916,166 A | 6/1999 | Reiss et al. |
| 5,921,924 A * | 7/1999 | Avitall ........................ 600/373 |
| 5,935,123 A | 8/1999 | Edwards et al. |
| 5,980,471 A | 11/1999 | Jafari |
| 5,980,504 A * | 11/1999 | Sharkey et al. ............. 604/508 |
| 5,993,424 A | 11/1999 | Lorenzo et al. |
| 6,004,319 A | 12/1999 | Goble et al. |
| 6,007,570 A | 12/1999 | Sharkey et al. |
| 6,014,579 A | 1/2000 | Pomeranz et al. |
| 6,023,638 A | 2/2000 | Swanson |
| 6,033,397 A | 3/2000 | Laufer et al. |
| 6,048,329 A | 4/2000 | Thompson et al. |
| 6,056,744 A | 5/2000 | Edwards |
| 6,073,051 A | 6/2000 | Sharkey et al. |
| 6,095,149 A | 8/2000 | Sharkey et al. |
| 6,099,514 A | 8/2000 | Sharkey et al. |
| 6,106,522 A | 8/2000 | Fleischman et al. |
| 6,122,549 A | 9/2000 | Sharkey et al. |
| 6,126,682 A | 10/2000 | Sharkey et al. |
| 6,135,999 A | 10/2000 | Fanton et al. |
| 6,165,139 A | 12/2000 | Damadian |
| 6,203,525 B1 * | 3/2001 | Whayne et al. ............. 604/528 |
| 6,217,528 B1 | 4/2001 | Koblish et al. |
| 6,224,592 B1 | 5/2001 | Eggers et al. |
| 6,241,754 B1 | 6/2001 | Swanson et al. |
| 6,245,061 B1 | 6/2001 | Panescu et al. |
| 6,258,086 B1 | 7/2001 | Ashley et al. |
| 6,261,311 B1 | 7/2001 | Sharkey et al. |
| 6,264,650 B1 | 7/2001 | Hovda et al. |
| 6,270,476 B1 | 8/2001 | Santoianni et al. |
| 6,273,886 B1 * | 8/2001 | Edwards et al. ............... 606/34 |
| 6,277,112 B1 | 8/2001 | Underwood et al. |
| 6,283,960 B1 | 9/2001 | Ashley |
| 6,290,715 B1 | 9/2001 | Sharkey et al. |
| 6,304,785 B1 | 10/2001 | McCreery et al. |
| 6,308,091 B1 * | 10/2001 | Avitall ........................ 600/374 |
| 6,332,880 B1 * | 12/2001 | Yang et al. .................. 604/528 |
| 6,355,032 B1 | 3/2002 | Hovda et al. |
| 6,416,508 B1 | 7/2002 | Eggers et al. |
| 6,428,512 B1 | 8/2002 | Anderson et al. |
| 6,440,127 B2 | 8/2002 | McGovern et al. |
| 6,440,129 B1 | 8/2002 | Simpson |
| 2001/0031963 A1 | 10/2001 | Sharkey et al. |
| 2001/0056278 A1 | 12/2001 | Nield et al. |
| 2002/0022830 A1 | 2/2002 | Sharkey et al. |
| 2002/0065541 A1 | 5/2002 | Fredricks et al. |
| 2002/0120259 A1 | 8/2002 | Lettice et al. |

FOREIGN PATENT DOCUMENTS

| | | |
|---|---|---|
| EP | 0439263 A1 | 7/1991 |
| EP | 0 479 482 | 4/1992 |
| EP | 0542412 A1 | 5/1993 |
| EP | 0 558 297 | 9/1993 |
| EP | 0572131 A1 | 12/1993 |
| EP | 0 682 910 | 11/1995 |
| EP | 0682910 A1 | 11/1995 |
| EP | 0729730 A1 | 9/1996 |
| GB | 1340451 | 12/1973 |
| WO | WO 82/02488 | 8/1982 |
| WO | WO 85/02762 | 7/1985 |
| WO | WO 92/05828 | 4/1992 |
| WO | WO 92/10142 | 6/1992 |

| | | |
|---|---|---|
| WO | WO 93/16648 | 9/1993 |
| WO | WO 93/20984 | 10/1993 |
| WO | WO 95/01814 | 1/1995 |
| WO | WO 95/10981 | 4/1995 |
| WO | WO 95/13113 | 5/1995 |
| WO | WO 95/18575 | 7/1995 |
| WO | WO 95/20360 | 8/1995 |
| WO | WO 95/25471 | 9/1995 |
| WO | WO 95/30377 | 11/1995 |
| WO | WO 95/34259 | 12/1995 |
| WO | WO 96/11638 | 4/1996 |
| WO | WO 96/34568 | 7/1996 |
| WO | WO 96/32051 | 10/1996 |
| WO | WO 96/32885 | 10/1996 |
| WO | WO 96/34559 | 11/1996 |
| WO | WO 96/34571 | 11/1996 |
| WO | WO 96/39914 | 12/1996 |
| WO | WO 97/06855 | 2/1997 |
| WO | WO 98/07468 | 2/1998 |
| WO | WO 98/17190 | 4/1998 |
| WO | WO 99/18878 | 4/1999 |
| WO | WO 99/47058 | 9/1999 |

OTHER PUBLICATIONS

Hugh Sharkey et al., "Intervertebral Disc Device Employing Prebent Sheath," filed Jun. 6, 2001, as U.S. patent application Ser. No. 09/876,827.

Hugh Sharkey et al., "Intervertebral Disc Device Employing Flexible Probe," filed Jun. 6, 2001, as U.S. patent application Ser. No. 09/876,832.

Andy Uchida et al., "Electromagnetic Energy Delivery Intervertebral Disc Treatment Devices," filed Jun. 6, 2001, as U.S. patent application Ser. No. 09/876,831.

"The Less–Invasive Laser Advantage," Product Brochure, Trimedyne.

"Two Physicians Perform First Outpatient Cervical Disc Procedure Using Laser Technology," Laser Centers of America Press Release dated Dec. 12, 1994 3 pages.

Attachment I: Competitive Literature on Generators with Bipolar Capabilities, brochures from Valleylab, Concept, and Zimmer.

Attachment II: Competitive Literature on Generators with Bipolar Forceps and Footswtich Controls, brochures from Weck Electrosurgery, Bard Electro Medical Systems and Valleylab.

Bosacco, S.J., et al., "Functional Results of Percutaneous Laser Discectomy," *The American Journal of Orthopedics*, Dec. 1996, pp. 825–828.

Bromm, B., and Treede, R.–D., "Nerve Fibre Discharges, Cerebral Potentials and Sensations Induced by $CO_2$ Laser Stimulation," *Human Neurobiology*, vol. 3, No. 1, 1984, pp. 33–40.

Buchelt, M., et al., "Erb: YAG and Hol: YAG Laser Ablation of Meniscus and Intervertebral Discs," *Lasers in Surgery and Medicine*, vol. 12, No. 4, 1992, pp. 375–381.

Buchelt, M., et al., "Fluorescence Guided Excimer Laser Ablation of Intervertebral Discs In Vitro," *Lasers In Surgery and Medicine*, vol. 11, 1991, pp. 280–286.

Choy, D.S.J., et al., "Percutaneous Laser Disc Decompression: A New Therapeutic Modality," *SPINE*, vol. 17, No. 8, 1992, pp. 949–956.

Christian, C.A., and Indelicato, P.A., "Allograft Anterior Cruciate Ligament Reconstruction with Patellar Tendon: An Endoscopic Technique," *Operative Techniques in Sports Medicine*, Vo.1, No. 1, Jan. 1993, pp. 50–57.

Cosman, E.R., and Cosman, B.J., "Methods of Making Nervous System Lesions," *Neurosurgery*, R.H. Wilkins and S.S. Rengachary, eds., Chapter 337, pp. 2490–2499.

Cosman, E.R., et al., "Theoretical Aspects of Radiofrequency Lesions in the Dorsal Root Entry Zone" *Neurosurgery*, Vo. 15, No. 6, 1984, pp. 945–950.

Cosset, J.M., "Resistive Radiofrequency (Low Frequency) Interstitial heating (RF Technique)," *Interstitial Hyperthermia*, Dec. 6, 1993, pp. 3–5 and 37–41.

Davis, J. K., "Early Experience with Laser Disc Decompression A Percutaneous Method," *Journal of the Florida Medical Association, Inc.*, vol. 79, No. 1, Jan. 1992, pp. 37–39.

Gehring, W.J., "Exploring the Homebox," *Gene*, vol. 135, 1993, pp. 215–221.

Gottlob, C., et al., "Holmium: YAG Laser Ablationof Human Intervertebral Disc: Preliminary Evaluation," *Lasers in Surgery and Medicine*, vol. 12, 1992, pp. 86–91.

Houpt, J.C., et al., "Experimental Study of Temperature Distributions and Thermal Transport During Radiofrequency Current Therapy of the Intervertebral Disc," *SPINE*, vol. 21, No. 15, pp. 1808–1813.

Kelly, L.E., "Purification and Properties of a 23 kDa $Ca^{2+}$-binding Protein from *Drosophila Melanogaster*, " *Biochem J.*, vol. 271, pp. 661–666.

Kolařik, J., et al., "Photonucleolysis of Intervertebral Disc and Its Herniation," *Zentralblatt für Neurochirurgie*, vol. 51, No. 2, 1990, pp. 69–71.

Leu, H. and Schreiber, A., "Endoskopie der Wirbelsäule: Minimal–Invasive Therapie," *Orthopäde*, vol. 21, No. 4, Aug. 1992, pp. 267–272.

Mayer, H.M., et al., "Lasers in Percutaneous Disc Surgery," Acta Orthopaedica Scandinavica Supplimentum 251, vol. 64, 1993, pp. 38–44.

McCulloch, J.A., and Organ, L.W., "Percutaneous Radiofrequency Lumbar Rhizolysis (Rhizotomy)," Canadian Medical Association Journal, vol. 116, No. 1, Jan. 8, 1977, pp. 30–33.

Mehta, M. and Sluijter, M.E., "the Treatment of Chronic Back Pain," *Anaesthesia*, vol. 34, No. 8, Sep. 1979, pp. 768–775.

Patil, A.A., et al., "Percutaneous Discectomy Using the Electromagnetic Field Focusin Probe. a Feasibility Study," *International Surgery*, vol. 76, 1991, pp. 30–32.

Phillips, J.J., et al., "MR Imaging of HO: YAG Laser Diskectomy with Histologic Correlation," *Journal of Magnetic Resonance Imaging*, vo. 3, No. 3, May/Jun. 1993, pp. 515–520.

Quigley, M.R., et al., "Laser Discectomy Comparison of Systems," *SPINE*, vol. 19, No. 3, Feb. 1, 1994, pp. 319–322.

Schatz, S.W., and Talalla, A., "Preliminary Experience with Percutaneous Laser Disc Decompression in the Treatment of Sciatica," *CJS–JCC*, vol. 38, No. 5, Oct. 1995, pp. 432–436.

Sluijter, M.E., "The Use of Radiofrequency Lesions for Pain Relief in Failed Back Patients," *Int Disabil Studies*, vol. 10, Sep. 4, 1996, pp. 37–43.

Sluijter, M.E., and Mehta, M., "Treatment of Chronic Back and Neck Pain by Percutaneous Thermal Lesions," *Persistent Pain: Modern Methods of Treatment*, vol. 3, Chapter 8, pp. 141–178, S. Lipton and J. Miles, eds., 1981.

Sluyter, M.E., "Radiofrequency Lesions in the Treatment of Cervical Pain Syndromes," *Radionics,* pp. 1–24, 1980.

Sminia, P., et al., "Effects of 434 MHz Microwave Hypothermia Applied to the Rat in the Region of Cervical Spinal Cord," *Int. J. Hyperthermia,* vo. 3, No. 5, 1987, pp. 441–452.

Troussier B., et al., "Percutaneous Intradiscal Radio–Frequency Thermocoagulation: A Cadaveric Study," *SPINE*, co. 20, No. 15, Aug. 1, 1995, pp. 1713–1718.

Vorwerk, V.D., et al., "Laserablation des Nucleus Pulposus: Optische Eigenshaften von Dengeriertem Bandscheibengewebe im Welleniängenberich von 200 bis 2200 nm," *RÖFÖ,* vol. 151, No. 6, Dec. 1989, pp. 647–790.

Wolgin, M., et al., "Excimer Ablation of Human Intervertebral Disc at 308 Nanometers," *Lasers in Surgery and Medicine,* vol. 9, No. 2, 1989, pp. 124–131.

Yonezawa T., et al., "The system and Procedures of Percutaneous Intradiscal Laser Nucleotomy," *SPINE (Japanese Edition)*, vol. 15, No. 11, 1990, pp. 1175–1185.

* cited by examiner

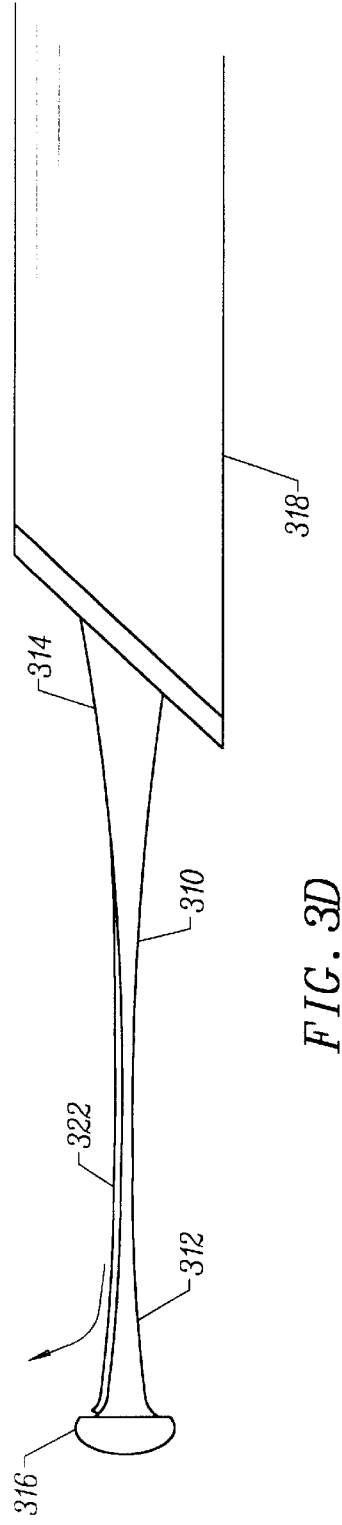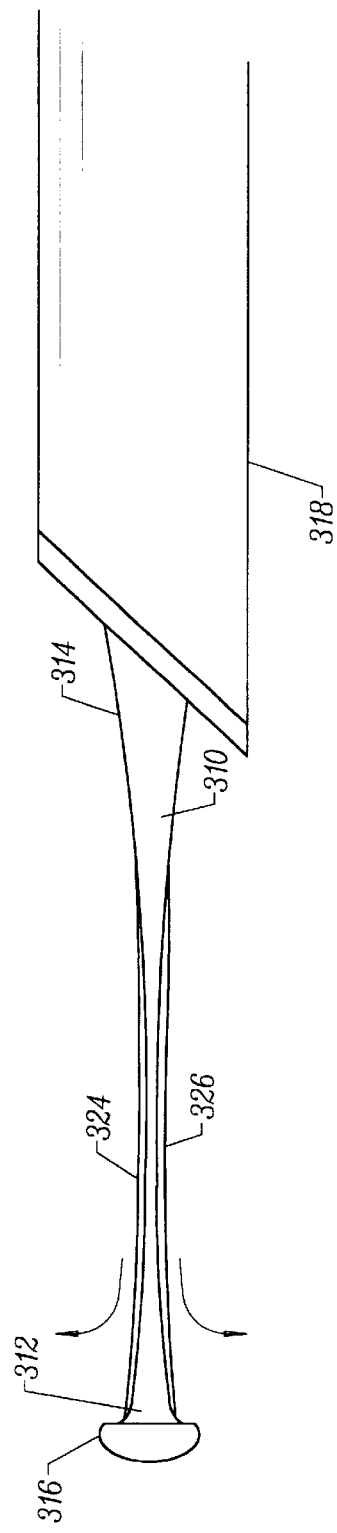

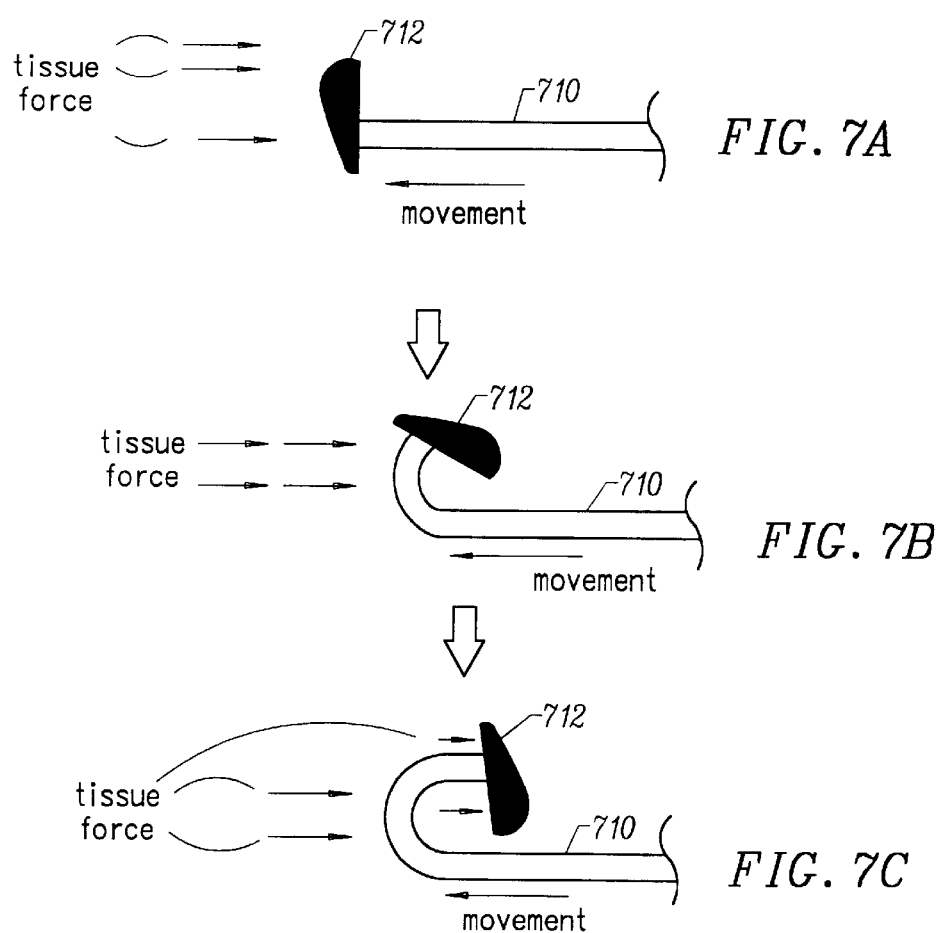

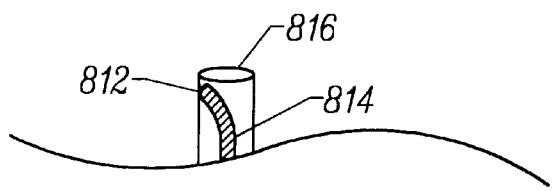
*FIG. 8A*
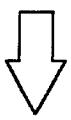
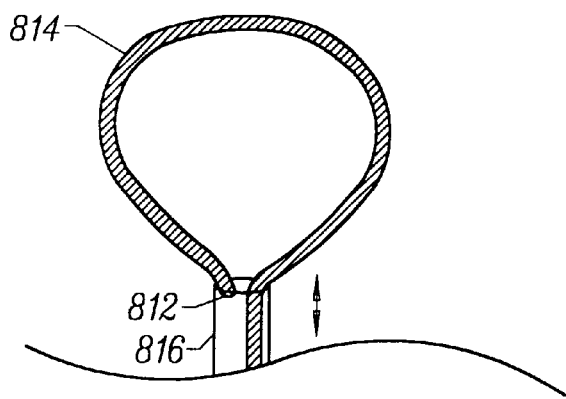
*FIG. 8B*

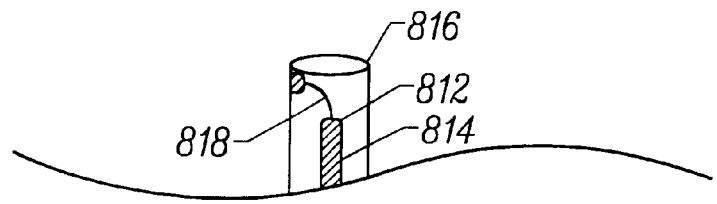
*FIG. 8C*
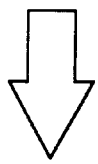
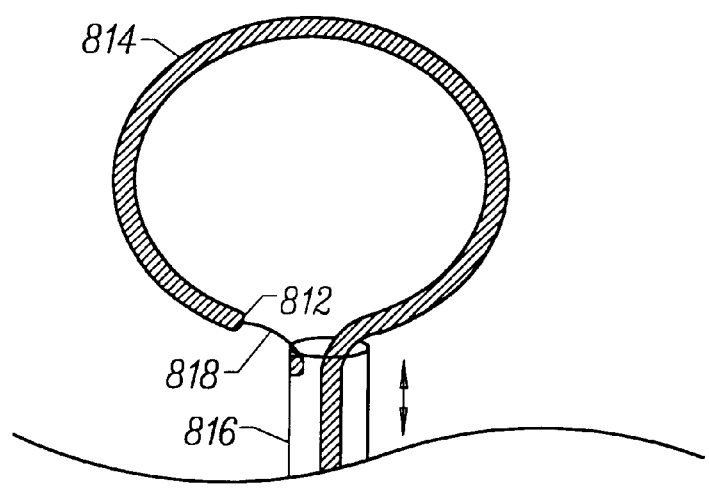
*FIG. 8D*

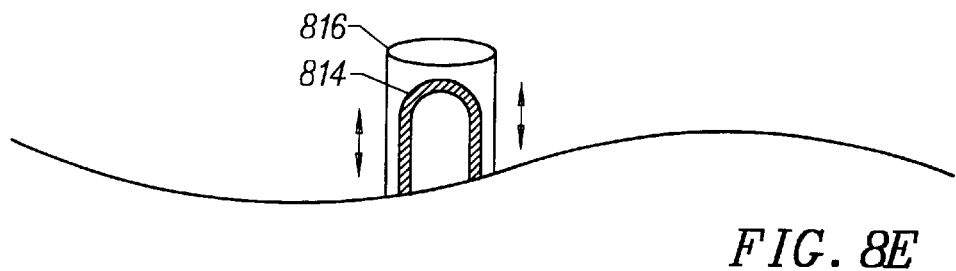
FIG. 8E
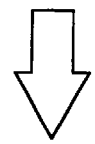
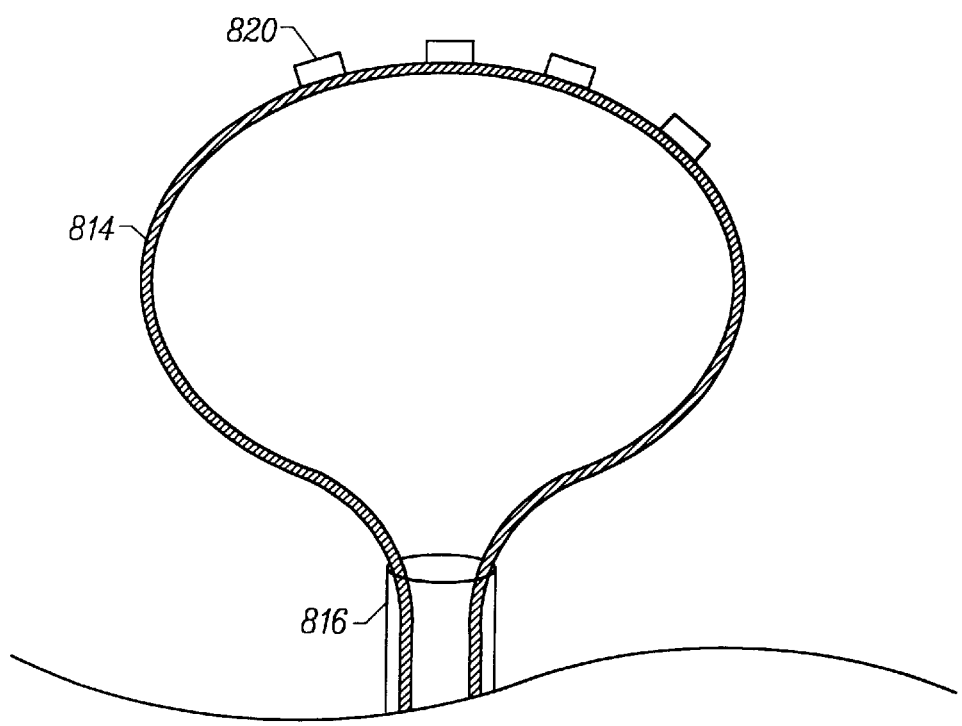
FIG. 8F

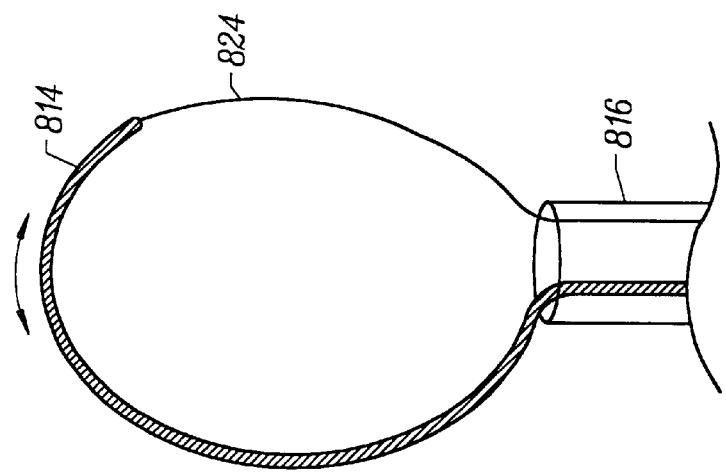
FIG. 8L
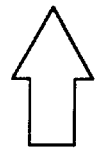
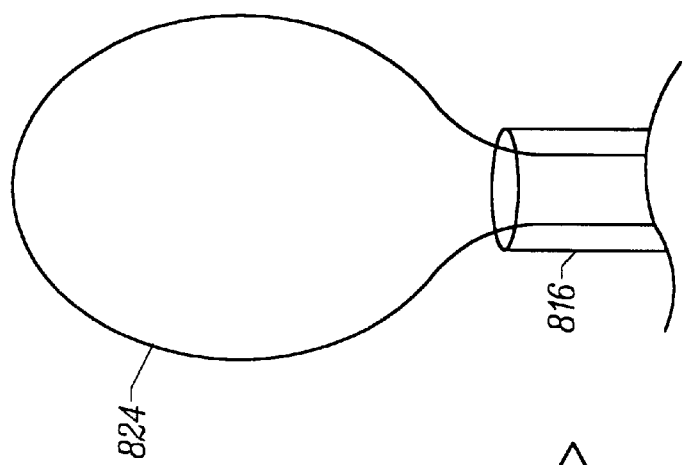
FIG. 8K
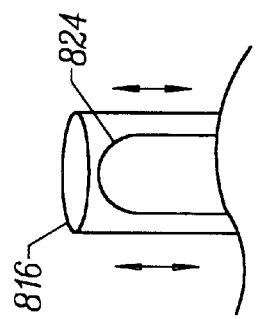
FIG. 8J

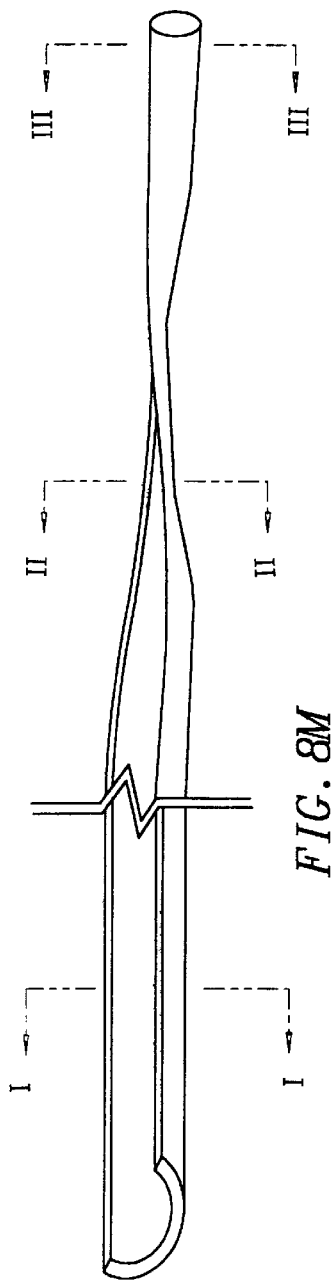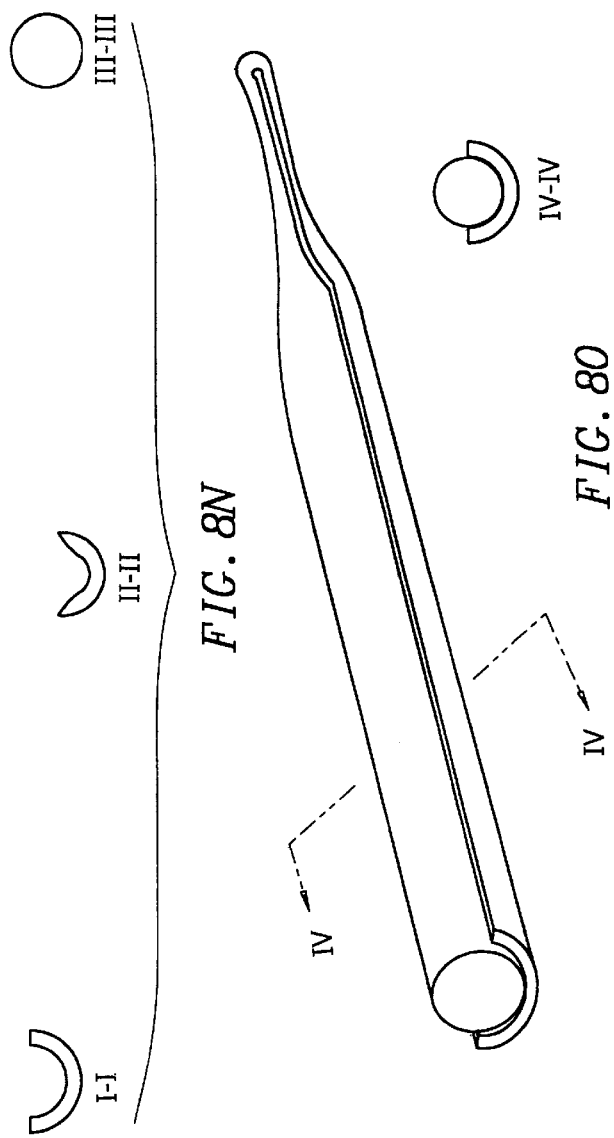
FIG. 8M
FIG. 8N
FIG. 8O

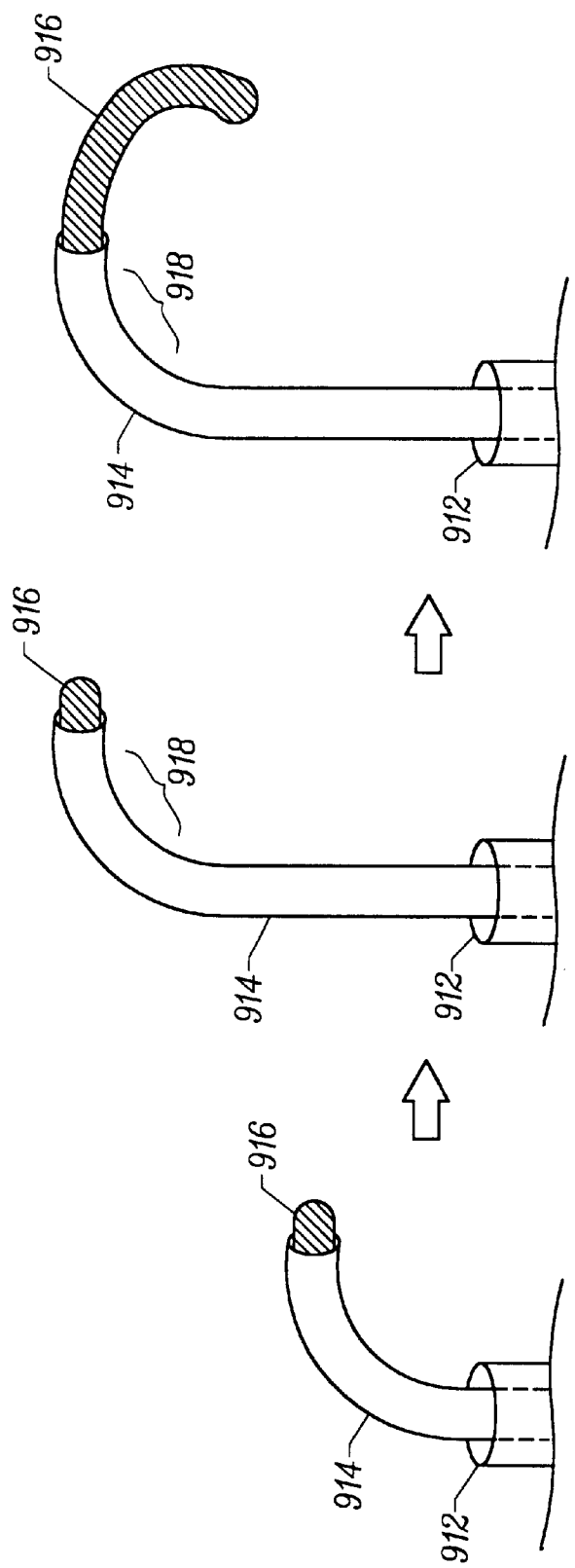

INTERVERTEBRAL DISC DEVICE EMPLOYING LOOPED PROBE

CROSS-REFERENCE TO RELATED APPLICATIONS

The present application relates to co-opending application Ser. No. 09/876,831, filed Jun. 6, 2001, to Andy Uchida et al., entitled "ELECTROMAGNETIC ENERGY DELIVERY INTERVERTEBRAL DISC TREATMENT DEVICES," pending, and to Ser. No. 09/876,832, filed Jun. 6, 2001, to Hugh Sharkey et al., entitled "INTERVERTEBRAL DISC DEVICE EMPLOYING FLEXIBLE PROBE," pending, and to Ser. No. 09/876,827, filed Jun. 6, 2001, to Hugh Sharkey et al., entitled "INTERVERTEBRAL DISC DEVICE EMPLOYING PREBENT SHEATH," pending.

BACKGROUND OF THE INVENTION

1. Field of the Invention

This invention relates to methods and apparatuses for accessing and modifying intervertebral disc tissue and more particularly to accessing and modifying intervertebral disc tissue using percutaneous techniques that avoid major surgical intervention.

2. Description of Related Art

Intervertebral disc abnormalities have a high incidence in the population and may result in pain and discomfort if they impinge on or irritate nerves. Disc abnormalities may be the result of trauma, repetitive use, metabolic disorders and the aging process and include such disorders but are not limited to degenerative discs (i) localized tears or fissures in the annulus fibrosus, (ii) localized disc herniations with contained or escaped extrusions, and (iii) chronic, circumferential bulging disc.

Disc fissures occur rather easily after structural degeneration (a part of the aging process that may be accelerated by trauma) of fibrous components of the annulus fibrosus. Sneezing, bending or just attrition can tear these degenerated annulus fibers, creating a fissure. The fissure may or may not be accompanied by extrusion of nucleus pulposus material into or beyond the annulus fibrosus. The fissure itself may be the sole morphological change, above and beyond generalized degenerative changes in the connective tissue of the disc. Even if there is no visible extrusion, biochemicals within the disc may still irritate surrounding structures. Disc fissures can be debilitatingly painful. Initial treatment is symptomatic, including bed rest, pain killers and muscle relaxants. More recently, spinal fusion with cages have been performed when conservative treatment did not relieve the pain. The fissure may also be associated with a herniation of that portion of the annulus.

With a contained disc herniation, there are no free nucleus fragments in the spinal canal. Nevertheless, even a contained disc herniation is problematic because the outward protrusion can press on the spinal nerves or irritate other structures. In addition to nerve root compression, escaped nucleus pulposus contents may chemically irritate neural structures. Current treatment methods include reduction of pressure on the annulus by removing some of the interior nucleus pulposus material by percutaneous nuclectomy. However, complications include disc space infection, nerve root injury, hematoma formation, instability of the adjacent vertebrae and collapse of the disc from decrease in height.

Another disc problem occurs when the disc bulges outward circumferentially in all directions and not just in one location. Over time, the disc weakens and takes on a "roll" shape or circumferential bulge. Mechanical stiffness of the joint is reduced and the joint may become unstable. One vertebra may settle on top of another. This problem continues as the body ages and accounts for shortened stature in old age. With the increasing life expectancy of the population, such degenerative disc disease and impairment of nerve function are becoming major public health problems. As the disc "roll" extends beyond the normal circumference, the disc height may be compromised, foramina with nerve roots are compressed. In addition, osteophytes may form on the outer surface of the disc roll and further encroach on the spinal canal and foramina through which nerves pass. The condition is called lumbar spondylosis.

It has been thought that such disc degeneration creates segmental instability which disturbs sensitive structures which in turn register pain. Traditional, conservative methods of treatment include bed rest, pain medication, physical therapy or steroid injection. Upon failure of conservative therapy, spinal pain (assumed to be due to instability) has been treated by spinal fusion, with or without instrumentation, which causes the vertebrae above and below the disc to grow solidly together and form a single, solid piece of bone. The procedure is carried out with or without discectomy. Other treatment include discectomy alone or disc decompression with or without fusion. Nuclectomy can be performed by removing some of the nucleus to reduce pressure on the annulus. However, complications include disc space infection, nerve root injury, hematoma formation, and instability of adjacent vertebrae.

These interventions have been problematic in that alleviation of back pain is unpredictable even if surgery appears successful. In attempts to overcome these difficulties, new fixation devices have been introduced to the market, including but not limited to pedicle screws and interbody fusion cages. Although pedicle screws provide a high fusion success rate, there is still no direct correlation between fusion success and patient improvement in function and pain. Studies on fusion have demonstrated success rate of between 50% and 67% for pain improvement, and a significant number of patients have more pain postoperatively. Therefore, different methods of helping patients with degenerative disc problems need to be explored.

One of the challenges associated with treating intervertebral discs is accessing them via percutaneous methods. To appreciate the difficulty presented, the anatomical structure of the spine and an intervertebral disc is illustrated and described below.

FIGS. 1A and 1B illustrate a cross-sectional anatomical view of a vertebra and associated disc and a lateral view of a portion of a lumbar and thoracic spine, respectively. Structures of a typical cervical vertebra (superior aspect) are shown in FIG. 1A: 104—lamina; 106—spinal cord; 108—dorsal root of spinal nerve; 114—ventral root of spinal nerve; 115—posterior longitudinal ligament; 118—intervertebral disc; 120—nucleus pulposus; 122—annulus fibrosus; 124—anterior longitudinal ligament; 126—vertebral body; 128—pedicle; 130—vertebral artery; 132—vertebral veins; 134—superior articular facet; 136—posterial lateral portion of the annulus; 138—posterior medial portion of the annulus; and 142—spinous process. In FIG. 1A, one side of the intervertebral disc 118 is not shown so that the anterior vertebral body 126 can be seen.

FIG. 1B is a lateral aspect of the lower portion of a typical spinal column showing the entire lumbar region and part of the thoracic region and displaying the following structures: 162—intervertebral disc; 142—spinous process; 168—inferior articular process; 170—inferior vertebral notch; 174—superior articular process; 176—lumbar curvature; and 180—sacrum.

The presence of the spinal cord and the posterior portion of the vertebral body, including the spinous process, and superior and inferior articular processes, prohibit introduction of a needle or trocar from a directly posterior position. This is important because the posterior disc wall is the site of symptomatic annulus tears and disc protrusions/extrusions that compress or irritate spinal nerves for most degenerative disc syndromes.

FIG. 1C provides a posterior-lateral anatomical view of two lumbar vertebrae and illustration of the triangular working zone. The inferior articular process 168, along with the pedicle 128 and the lumbar spinal nerve 110, form a small "triangular" window through which introduction of an instrument can be achieved from the posterior lateral approach. FIG. 1D illustrates an instrument (an introducer 169) introduced into an intervertebral disc by the posterior lateral approach.

FIG. 1E illustrates the anatomy of an intervertebral disc in greater detail and shows an introducer 169 inserted into the disc. Structures of the disc are identified and described by these anatomical designations: the posterior lateral inner annulus 136, posterior medial inner annulus 138, annulus fibrosus 122/nucleus pulposus 120 interface, the annulus/dural interface 146, annulus/posterior longitudinal ligament interface 148, anterior lateral inner annulus 150, and the anterior medial inner annulus 152.

The annulus fibrosus 122 is comprised primarily of tough fibrous material, while the nucleus pulposus 120 is comprised primarily of an amorphous colloidal gel. There is a transition zone between the annulus fibrosus 122 and the nucleus pulposus 120 made of both fibrous-like material and amorphous colloidal gel. The border between the annulus fibrosus 122 and the nucleus pulposus 120 becomes more difficult to distinguish as a patient ages, due to degenerative changes. This process may begin as early as 30 years of age. For purposes of this specification, the inner wall of the annulus fibrosus can include the young wall comprised primarily of fibrous material as well as the transition zone which includes both fibrous material and amorphous colloidal gels (hereafter collectively referred to as the "inner wall of the annulus fibrosus"). Functionally, the location at which there is an increase in resistance to probe penetration and which is sufficient to cause bending of the distal portion of the probe into a radius less than that of the internal wall 22 of the annulus fibrosus is considered to be the "inner wall of the annulus fibrosus".

As with any medical instrument and method, not all patients can be treated, especially when their disease or injury is too severe. There is a medical gradation of degenerative disc disease (stages 1–5). See, for example, Adams et al., "The Stages of Disc Degeneration as Revealed by Discograms," J. Bone and Joint Surgery, 68, 36–41 (1986). As these grades are commonly understood, the methods of instrument navigation described herein would probably not be able to distinguish between the nucleus and the annulus in degenerative disease of grade 5. In any case, most treatment is expected to be performed in discs in stages 3 and 4, as stages 1 and 2 are asymptomatic in most patients, and stage 5 may require disc removal and fusion.

It is well known to those skilled in the art that percutaneous access to the disc is achieved by placing an introducer into the disc from this posterior lateral approach, but the triangular window does not allow much room to maneuver. Once the introducer pierces the tough annulus fibrosus, the introducer is fixed at two points along its length and has very little freedom of movement. Thus, with the exception of devices such as those described in U.S. Pat. Nos. 6,135,999; 6,126,682; 6,122,549; 6,099,514; 6,095,149; 6,073,051; 6,007,570; 5,980,504 (which are each incorporated herein by reference), the posterior lateral approach has only allowed access to small central and anterior portions of the nucleus pulposus.

The present invention provides devices and methods which are designed to more efficiently access and treat the interior of intervertebral discs by the posterior lateral approach.

SUMMARY OF THE INVENTION

The present invention relates to various embodiments of intervertebral disc devices and their methods of use.

According to one embodiment, the intervertebral disc device comprises a distal probe sized to be extended from a distal end of an introducer that is percutaneously delivered into an interior of an intervertebral disc, a distal section of the probe comprising a flexible neck which tapers in a proximal to distal direction, and a distal tip which is larger in cross sectional diameter than the flexible neck adjacent the distal tip, the flexible neck and distal tip serving to prevent the probe distal end from piercing an internal wall of the intervertebral disc; and a proximal handle for externally guiding the probe within an intervertebral disc.

The flexible neck may optionally be designed such that it is not predisposed to bending in any direction relative to a longitudinal axis of the probe. Alternatively, the flexible neck may be designed to be predisposed to bending along a single plane relative to a longitudinal axis of the probe. Alternatively, the flexible neck may be designed to be predisposed to bending in opposing directions along a single plane relative to a longitudinal axis of the probe. Alternatively, the flexible neck may be designed to be predisposed to bending in at least two different directions along at least two different planes relative to a longitudinal axis of the probe.

According to this embodiment, the flexible neck may optionally have a round cross section. Alternatively, or in addition, the flexible neck may optionally have at least one flat surface extending along a longitudinal axis of the neck. In one variation, the flexible neck has two flat surfaces extending along a longitudinal axis of the neck on opposing sides of the neck.

Also according to this embodiment, the neck may optionally be formed of a flexible coil.

According to this embodiment, the distal tip may optionally have a larger cross sectional diameter than a largest cross sectional diameter of the flexible neck. The distal tip may be symmetrical or asymmetrical. In certain variations, the distal tip is dome shaped or has a flat surface perpendicular to a longitudinal axis of the probe.

The distal tip may be attached to the neck of the probe by a variety of mechanisms including, for example, a spring or a pivot mechanism such as a ball and socket mechanism.

In one preferred variation, the flexibility of the neck of the probe is designed such that it causes the probe to bend and the distal tip to trail behind a portion of the probe as the probe is advanced through tissue within an intervertebral disc. The shape of the distal tip may also contribute to the distal tip trailing behind a portion of the probe.

In another embodiment, an intervertebral disc device is provided comprising: a distal probe sized to be extended from a distal end of an introducer that is percutaneously delivered into an interior of an intervertebral disc, a distal section of the probe comprising an active electrode and a return electrode which are each spirally wrapped around the probe such that there are multiple alternating bands of the same active and return electrodes positioned longitudinally along the length of the distal section of the probe, the active and return electrodes being adapted to deliver bipolar electromagnetic energy to tissue within the intervertebral disc; and a proximal handle for externally guiding the probe within an intervertebral disc.

According to this embodiment, the distal section of the probe may be predisposed to forming a loop.

In another embodiment, an intervertebral disc device is provided comprising: a distal probe sized to be extended from a distal end of an introducer that is percutaneously delivered into an interior of an intervertebral disc, a distal section of the probe being predisposed to forming a loop when extended from the distal end of the introducer, the looping portion of the probe comprising an active electrode and a return electrode which are positioned on the probe such that the active and return electrodes are on opposing sides of the probe loop; and a proximal handle for externally guiding the probe within an intervertebral disc.

In yet another embodiment, an intervertebral disc device is provided comprising: a distal probe sized to be extended from a distal end of an introducer that is percutaneously delivered into an interior of an intervertebral disc, a distal section of the probe comprising separate active and return electrode elements which are predisposed to bending away from each other when extended from the distal end of the introducer; and a proximal handle for externally guiding the probe within an intervertebral disc.

In another embodiment, an intervertebral disc device is provided comprising: a distal sheath sized to be extended from a distal end of an introducer that is percutaneously delivered into an interior of an intervertebral disc, a distal section of the sheath being predisposed to adopting a bent configuration when extended from the introducer; a probe adapted to be extended from a distal end of the sheath, the bent section of the sheath causing the probe to adopt a same bent configuration; and a proximal handle for externally guiding the probe within an intervertebral disc.

In another embodiment, an intervertebral disc device is provided comprising: a distal sheath sized to be extended from a distal end of an introducer that is percutaneously delivered into an interior of an intervertebral disc, a distal section of the sheath being predisposed to adopting a bent configuration when extended from the introducer; a guide wire adapted to be extended from a distal end of the sheath, the bent section of the sheath causing the guide wire to adopt a same bent configuration; a probe adapted to be extended from a distal end of the sheath over the guide wire, the bent section of the sheath causing the probe to adopt a same bent configuration; and a proximal handle for externally guiding the probe within an intervertebral disc.

According to one variation of this embodiment, a distal section of the probe comprises an active electrode and a return electrode which are each spirally wrapped around the probe such that there are multiple alternating bands of the same active and return electrodes positioned longitudinally along the length of the distal section of the probe, the active and return electrodes being adapted to deliver bipolar electromagnetic energy to tissue within the intervertebral disc.

Optionally, the distal section of the probe may be predisposed to forming a loop. When the distal section of the probe is predisposed to forming a loop when extended from the distal end of the introducer, the looping portion of the probe may comprise an active electrode and a return electrode which are positioned on the probe such that the active and return electrodes are on opposing sides of the probe loop.

According to another variation of this embodiment, a distal section of the probe comprises separate active and return electrode elements which are predisposed to bending away from each other when extended from the distal end of the introducer.

In another embodiment, an intervertebral disc device is provided comprising: a probe capable of being extended from a distal end of an introducer that is percutaneously delivered into an interior of an intervertebral disc, the probe forming a loop when extended from the distal end of the introducer, the loop having first and second proximal ends external to the introducer which are brought together adjacent the introducer distal end to form the loop by the proximal ends being either attached to or entering the distal end of the introducer; and a proximal handle for externally causing the probe to be extended from the distal end of the introducer and externally guiding the probe within an intervertebral disc.

According to this embodiment, the device may optionally further include an introducer, the first proximal end of the probe being attached to the introducer adjacent a distal end of the introducer, the second proximal end of the probe being extendable from the introducer distal end to form the loop. According to this variation, the first proximal end of the probe may optionally be attached to the introducer adjacent the distal end of the introducer by a guide wire lead. Alternatively, the first and second proximal ends of the probe may each be separately extendable from the introducer distal end to form the loop. When the first and second proximal ends of the probe are each separately extendable from the introducer distal end to form the loop, the first and second proximal ends of the probe may have different cross sectional geometries. According to this variation, the different cross sectional geometries of the first and second proximal ends may be selected such that the cross sectional geometry of the first proximal end is a compliment of the cross sectional geometry of the second proximal end.

In another embodiment, an intervertebral disc device is provided comprising: a guide wire capable of being extended from a distal end of an introducer that is percutaneously delivered into an interior of an intervertebral disc, the guide wire forming a loop when extended from the distal end of the introducer, the loop having first and second proximal ends external to the introducer which are brought together adjacent the introducer distal end to form the loop by the proximal ends being either attached to or entering the distal end of the introducer; a probe capable of being extended over the guide wire from the distal end of the introducer; and a proximal handle for externally causing the guide wire and probe to be extended from the distal end of the introducer and externally guiding the guide wire and probe within an intervertebral disc.

In one variation of this embodiment, the device further includes an introducer, the first proximal end of the guide wire being attached to the introducer adjacent a distal end of the introducer, the second proximal end of the guide wire being extendable from the introducer distal end to form the loop. In another variation, the first and second proximal ends of the guide wire are each separately extendable from the introducer distal end to form the loop.

In another embodiment, an intervertebral disc device is provided comprising: guide wire capable of being extended from a distal end of an introducer that is percutaneously delivered into an interior of an intervertebral disc, a distal section of the guide wire being predisposed to forming a loop when extended from the distal end of the introducer, the looped distal section of the guide wire serving to localize the looped distal section within the intervertebral disc; a probe capable of being extended over the guide wire from the distal end of the introducer, the probe and guide wire being extendable in combination such that position of the looped distal section of the guide wire is not changed; and a proximal handle for externally causing the guide wire and probe to be extended from the distal end of the introducer and externally guiding the guide wire and probe within an intervertebral disc.

According to any of the above embodiments, the device may further include flexible tubing operably interconnecting the proximal handle with the distal probe. The probe and/or guide wire may optionally extend within the flexible tubing to the handle.

Also according to any of the above embodiments, the device may further include a connector system which enables an introducer to be removeably attached to the connector system, the probe being positionable within the introducer for delivery within the intervertebral disc with the assistance of the introducer.

According to any of the above embodiments, the device may further include a probe or guide wire with a mechanism for securing the probe or guide wire within the selected section of the intervertebral disc. The mechanism may be a curved portion adjacent the distal end capable of anchoring the probe or guide wire into tissue. The curved distal portion preferably forms a distal end of the probe or guide wire. The curved distal portion is optionally retractable and optionally divides into multiple separate curved portions, such as to form a treble hook.

Also according to any of the above embodiments, the probe may further include a functional element which performs a function. A wide variety of functions may be performed by the functional element including, but not limited to, transmitting energy to tissue within an intervertebral disc, delivering material to within an intervertebral disc, and removing material within an intervertebral disc.

When the function element transmits energy, the probe may further include an electromagnetic energy device capable of supplying energy within the intervertebral disc. The electromagnetic energy device may be capable of delivering energy selected from group consisting of coherent and incoherent light and radiofrequency (RF), microwave, and ultrasound waves. When delivering RF energy, the electromagnetic energy device comprises electrodes adapted to deliver RF energy. The RF electrodes may adopt a monopolar or bipolar configuration. The electromagnetic energy device may also comprise a resistive heating mechanism.

Also according to any of the above embodiments, the handle may further comprise a probe control element for controlling the movement of the probe adjacent a distal end of the device. The device may also comprise a guide wire control element for controlling the movement of the guide wire adjacent a distal end of the device.

Methods are also provided for employing the various devices of the present invention to treat an interior of an intervertebral disc.

In one embodiment, the method comprises inserting an introducer through a skin of a person such that the distal end of the introducer travels within the person via a posterior lateral approach to an intervertebral disc such that a distal end of the introducer is positioned in or adjacent an intervertebral disc; extending a probe from a distal end of the introducer such that the probe is positioned within the intervertebral disc; and treating tissue within the interior of the intervertebral disc using the probe. The probe that is extended from the introducer may have any of the various probe designs described herein.

In another embodiment, the method comprises inserting an introducer through a skin of a person such that the distal end of the introducer travels within the person via a posterior lateral approach to an intervertebral disc such that a distal end of the introducer is positioned in or adjacent an intervertebral disc; extending a guide wire from a distal end of the introducer such that the guide wire is positioned within the intervertebral disc; extending a probe over the guide wire, and treating tissue within the interior of the intervertebral disc using the probe. The guide wire and probe that are extended from the introducer may have any of the various guide wire and probe designs described herein.

In another embodiment of the invention, a method for delivering a probe is provided. The method comprises extending a guide wire into an intervertebral disc such that the guide wire is positioned within the intervertebral disc adjacent an inner wall of the disc; attaching a distal portion of the guide wire to the inner wall; and extending a probe over the guide wire. The guide wire and probe that are extended may have any of the various guide wire and probe designs described herein.

According to this embodiment, the step of attaching the distal portion of the guide wire may be accomplished by inserting a portion of the guide wire into the tissue of the inner wall of an intervertebral disc such that the distal portion is held in place and retained by the tissue of the inner wall of the disc. In this regard, a variety of attachment mechanisms may be employed. For attachment mechanism into the tissue of the inner wall of the disc. The attachment mechanism example, the step of attaching the distal portion of the guide wire may be by hooking the may be a curved distal portion of the guide wire.

All of the above embodiments involving attaching the guide wire to the inner wall of an intervertebral disc may be adapted where the probe instead of the guide wire comprises an attachment mechanism for attaching the probe to the inner wall.

BRIEF DESCRIPTION OF THE FIGURES

FIG. 3D illustrates a neck which has been flattened on one side.

FIG. 3E illustrates a neck which has been flattened on two opposing sides.

FIG. 4A illustrates a dome shaped distal tip where the distal tip is symmetrical about the longitudinal axis of the distal section of the probe.

FIG. 4B illustrates an offset dome shaped distal tip where the distal tip is asymmetrical about the longitudinal axis of the distal section of the probe.

FIG. 4C illustrates an flat distal tip.

FIG. 5A illustrates an embodiment where the distal tip and the neck of the distal section is one unit made of the same material.

FIG. 5B illustrates an embodiment where the distal tip and the neck of the distal section are attached to each other by a pivot mechanism.

FIG. 5C illustrates an embodiment where the distal tip and the neck of the distal section are attached to each other by a spring.

FIGS. 7A–7C illustrate a sequence which shows how tissue force resisting the forward advancement of the probe within the intervertebral disc causes the distal section of the probe to bend.

FIG. 7A shows a probe with an asymmetrical distal tip.

FIG. 7B illustrates that the asymmetrical resistance causes the distal section of the probe to bend.

FIG. 7C illustrates that further bending of the probe causes tissue force to be applied to the back of the distal tip as the distal section is advanced further.

FIG. 8A illustrates an embodiment where the distal end of the probe is attached to the distal end of the introducer.

FIG. 8M illustrates the guide wire unfolded where section I includes a guide wire with a thin, concave shape, section II includes a tapered section that provides an area where the guide wire is folded upon itself, and section III includes a rounded section such that the rounded section fits within the concave shape of section I.

FIG. 8N shows the cross sections of guide wire sections I–III illustrated in FIG. 8M.

FIG. 8O illustrates that the guide wire may be folded upon itself where the crease is at section II, and section I and section III come together.

FIG. 8Q illustrates yet another embodiment where a guide wire and probe are used in combination to deploy the probe adjacent an internal wall of a disc.

FIGS. 9A–9C illustrate one embodiment where a sheath having a predefined curvature adjacent its distal end introduces curvature to a guide wire or probe extended from the sheath.

FIG. 9A illustrates the distal end of an introducer with a sheath and a probe extending from the introducer.

FIG. 9B illustrates the sheath being extend from the distal end of the introducer.

FIG. 9C illustrates the probe being extended beyond the sheath.

FIG. 10A illustrates an embodiment where the thermal energy delivery device is a bipolar electrode comprising an active electrode and a return electrode where the active and return electrodes are each spirally wrapped around a portion of the distal section of the probe.

FIG. 10B illustrates another embodiment of a thermal energy delivery device where the active and return electrodes are positioned on opposing sides of the loop.

FIG. 10C illustrates another embodiment of a thermal energy delivery device.

FIG. 11A illustrates an embodiment where a pair of probes which form a return electrode and an active electrode extend from an introducer or sheath and are spaced apart from each other.

FIG. 11B illustrates a variation on the embodiment shown in FIG. 11A where the pair of probes which form an active electrode and return electrode diverge from each other adjacent their distal ends.

DETAILED DESCRIPTION

The present invention provides methods and devices for accessing and treating intervertebral discs. In general, the devices according to the present invention are externally guidable percutaneous intervertebral disc devices. As such, these devices are used to traverse the patent's skin and access an intervertebral disc through the tissue positioned between the patient's skin and the intervertebral disc. Entry into the intervertebral disc is achieved by a posterior lateral approach.

1. Overview of the Intervertebral Disc Treatment Device

Figure 2:
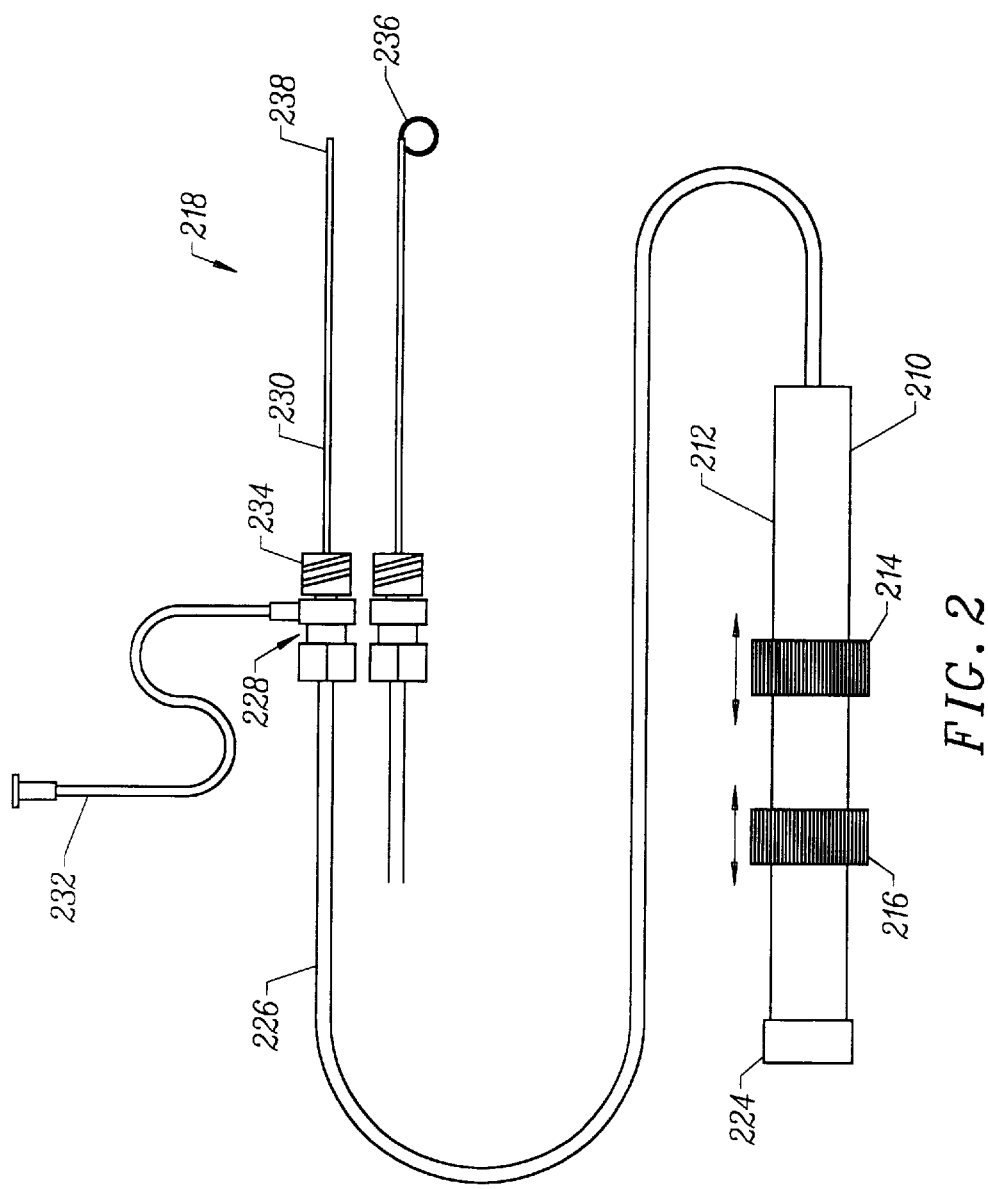
FIG. 2 illustrates an embodiment of an intervertebral disc device system.

FIG. 2 illustrates an embodiment of an overall system for treating intervertebral discs which incorporates devices of the present invention. It is noted that many of the subcomponents of the devices of the present invention, as well as their operation are described in further detail in U.S. Pat. Nos. 6,135,999; 6,126,682; 6,122,549; 6,099,514; 6,095,149; 6,073,051; 6,007,570; 5,980,504, which are each incorporated herein by reference.

FIG. 2 depicts but one embodiment of the overall system. It should be noted that systems incorporating the devices of the invention can be prepared in a number of different forms and can consist (for example) of a single instrument with multiple internal parts or a series of instruments that can be replaceably and sequentially inserted into a hollow fixed instrument (such as a needle) that guides the operational instruments to a selected location within the intervertebral disc. Because prior patents do not fully agree on how to describe parts of percutaneous instruments, terminology with the widest common usage will be used.

As illustrated in FIG. 2, the proximal end 210 of the system comprises a handle 212 which includes a guide wire control element 214 for controlling the movement of a guide wire adjacent a distal end 218 of the device and a probe body control element 216 for controlling the movement of a probe (not shown) adjacent the distal end 218 of the device. The handle 212 further includes one or more mechanisms 224 (not shown in detail) for attaching different external tools (e.g., energy sources, material delivery and removal mechanisms (e.g., a pump), visualization tools, etc.) to the device.

Flexible tubing 226 attaches the handle 212 to a connector system 228 which remains external to the body. As illustrated, the connector system 228 may allow different external tools to be attached to the device. In this case a fluid injection tool 232 is depicted. A probe and a guide wire may optionally extend from a distal portion of the device through the flexible tubing to the handle. Alternatively, only mechanisms for controlling the probe and guide wire may extend from the distal portion of the device through the flexible tubing to the handle.

Insertion of flexible tubing between the handle 212 and the connector system 228 serves to physically isolate movements of the handle 212 from the portion of the device which is inserted into the patient. As a result, the patient is less prone to perceive a manipulation of the device within the patient as a result of movement of the handle.

The distal portion of the devices of the present invention may be delivered through the skin of a patient and into an intervertebral disc using techniques typical of percutaneous interventions. The connector system 228 allows an introducer 230 to be removably coupled to the device to facilitate delivery of the distal portion of the device through a patient's skin to within an intervertebral disc. As illustrated, a luer fitting 234 may be used as the attachment mechanism for the introducer.

The term introducer is used herein to indicate that the device of the invention can be used with any insertional apparatus that provides proximity to the disc, including many such insertional apparatuses known in the art. An introducer has an internal introducer lumen with a distal opening 238 at a terminus of the introducer to allow insertion (and manipulation) of the operational parts of the device into (and in) the interior of a disc.

The introducer, in its simplest form, can consist of a hollow needle-like device (optionally fitted with an internal removable obturator or trocar to prevent clogging during initial insertion) or a combination of a simple exterior cannula that fits around a trocar. The result is essentially the same: placement of a hollow tube (the needle or exterior cannula after removal of the obturator or trocar, respectively) through skin and tissue to provide access into the annulus fibrosus. The hollow introducer acts as a guide for introducing instrumentation. More complex variations exist in percutaneous instruments designed for other parts of the body and can be applied to design of instruments intended for disc operations. Examples of such obturators are well known in the art. A particularly preferred introducer is a 17- or 18-gauge, thin-wall needle with a matched obturator, which after insertion is replaced with a probe of the present invention.

The devices of the present invention further include a probe 236 which may be extended and retracted relative to the distal opening 238 of the introducer 230. For example, a distal section of the probe 236 is shown to be retracted into the introducer in FIG. 2 (above) as well as extended from the distal end of the introducer (below). When extended from the introducer 230, the probe 236 is intended to be located inside the disc.

Figure 1A:
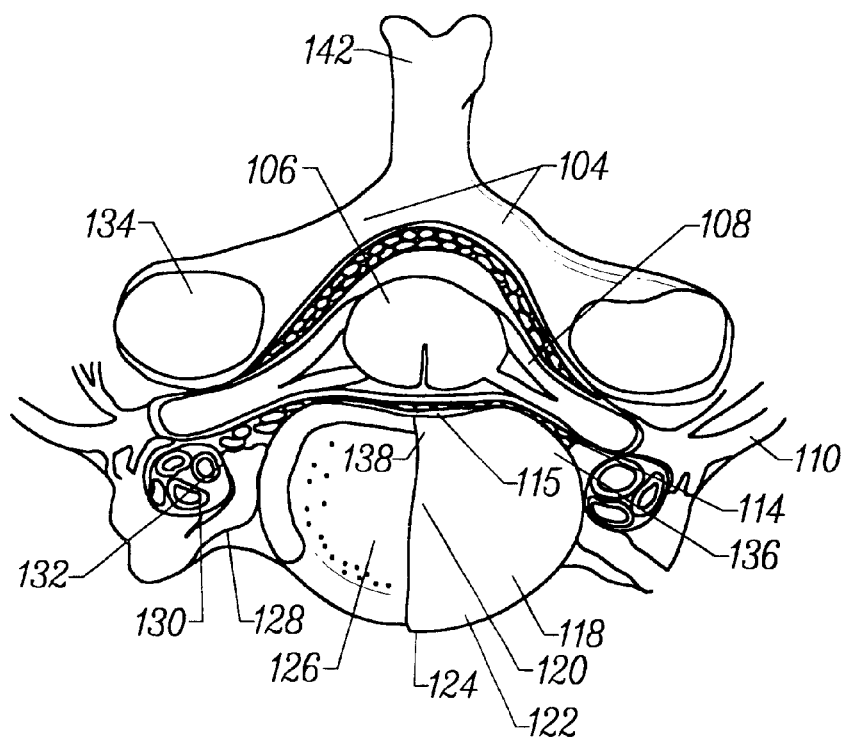
FIG. 1A provides a superior cross-sectional anatomical view of a cervical disc and vertebra.
Figure 1B:
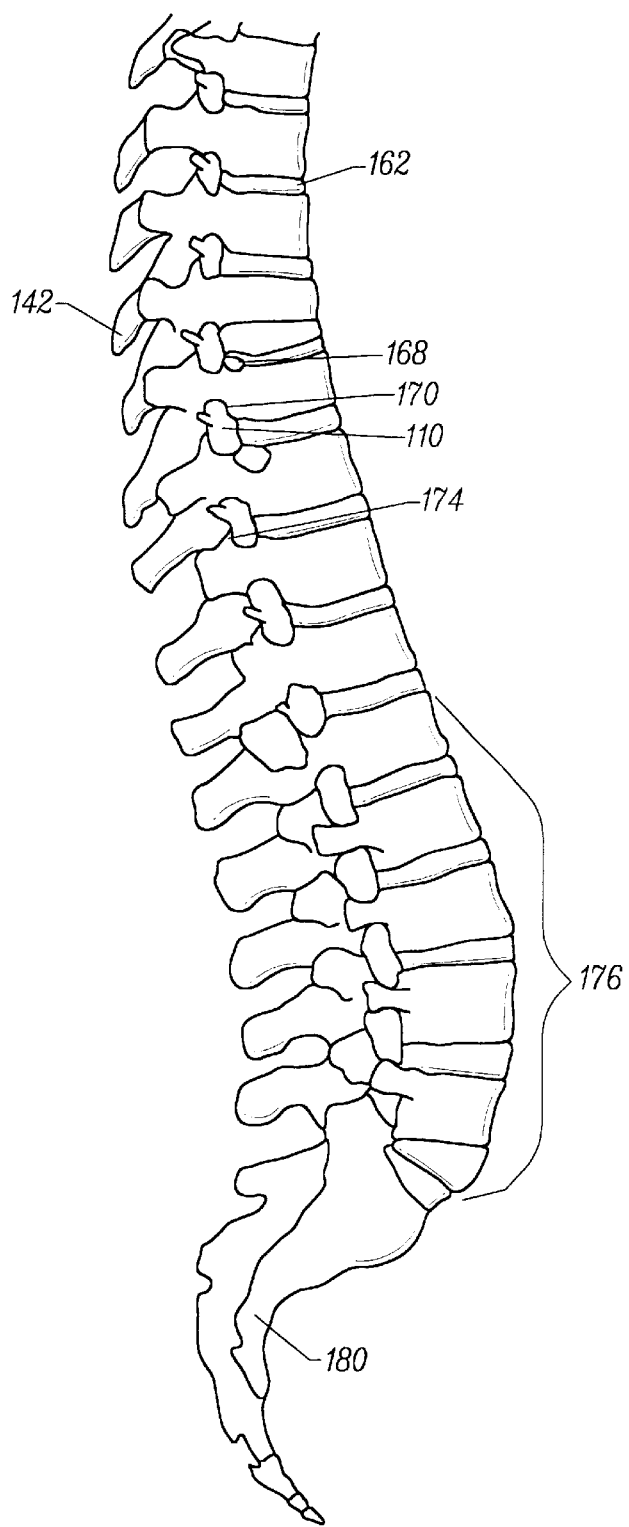
FIG. 1B provides a lateral anatomical view of a portion of a lumbar spine.
Figure 1D:
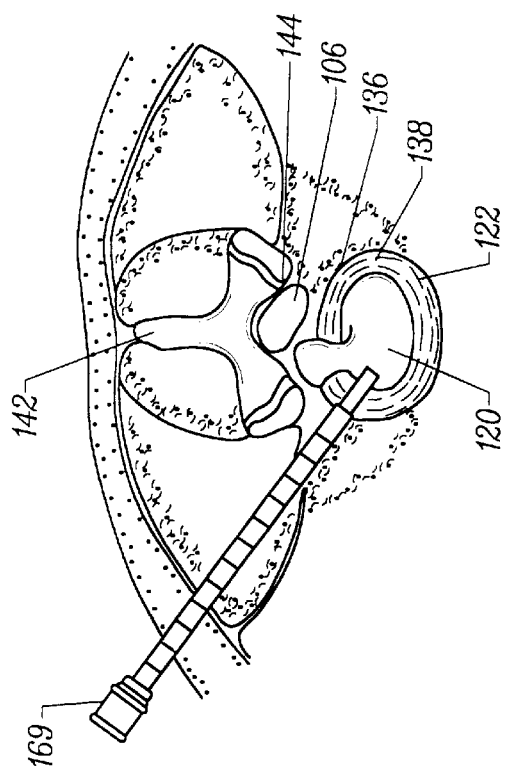
FIG. 1D provides a superior cross-sectional view of the required posterior lateral approach.
Figure 1C:
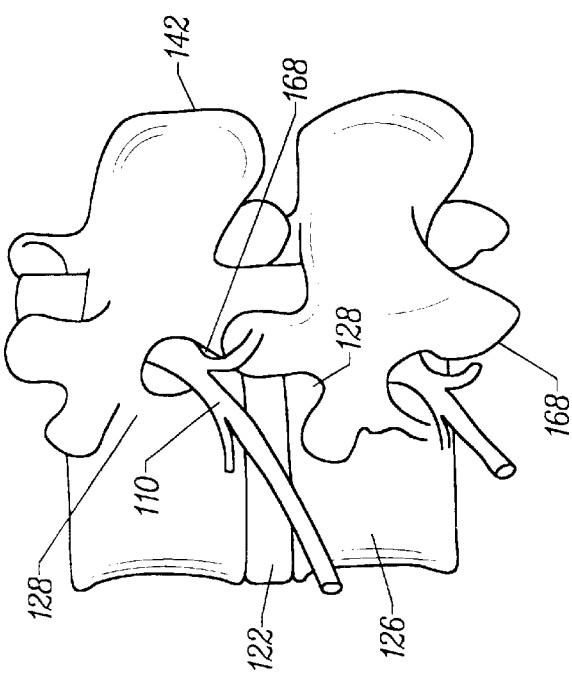
FIG. 1C provides a posterior-lateral anatomical view of two lumbar vertebrae and illustration of the triangular working zone.
Figure 1E:
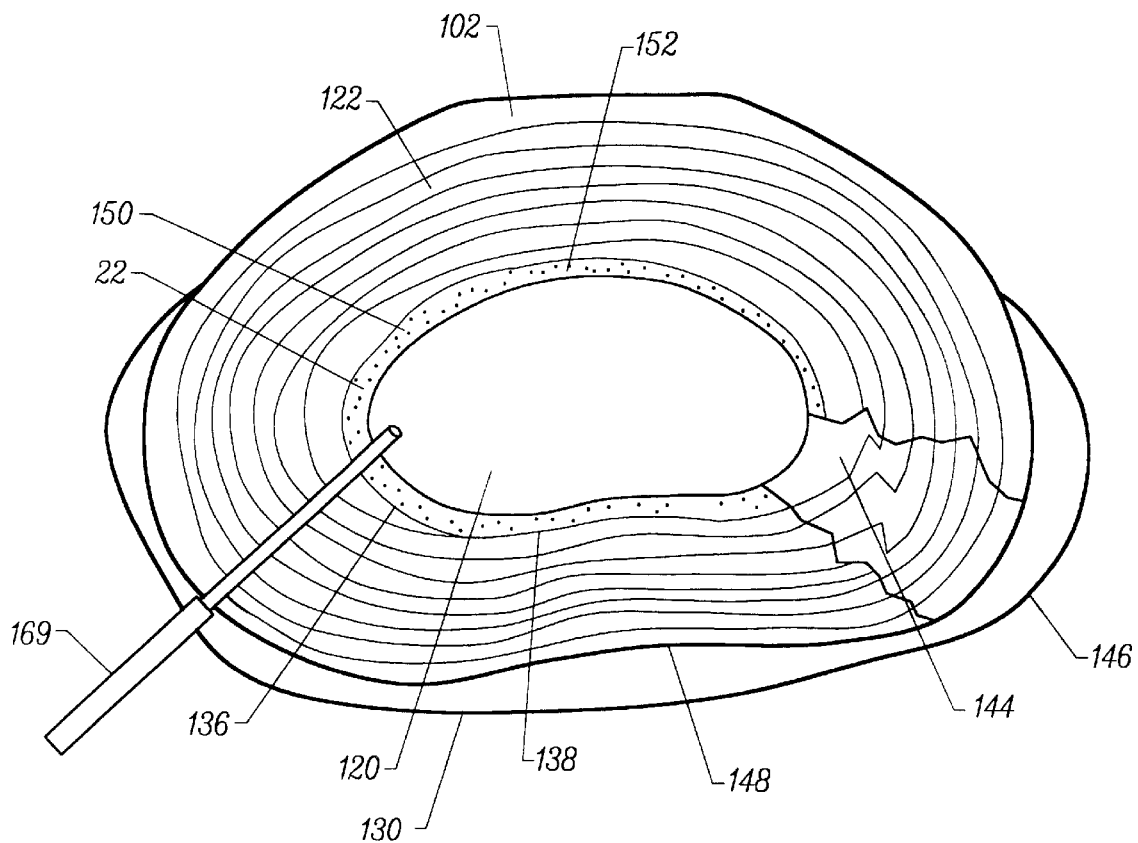
FIG. 1E illustrates the anatomy of an intervertebral disc in greater detail and shows an introducer inserted into the disc.

As illustrated in FIG. 1E, the introducer 169 pierces the annulus fibrosus 122 and is advanced through the wall of the annulus fibrosus into the nucleus pulposus 120. The introducer 169 is extended a desired distance into nucleus pulposus 120. Once the introducer 169 is positioned within the nucleus pulposus 120, the distal section of the probe 236 is advanced through a distal end of introducer 169 into nucleus pulposus 120.

It is noted that many probe devices access a section of tissue in the patient's body by being delivered within the lumen of a body vessel such as a vein or artery. Although the devices of the present invention are said to include a probe, the devices of the present invention do not rely upon accessing a section of tissue in the patient's body by being delivered within the lumen of a body vessel. Rather, "probe" is used herein to describe the distal portion of the device which is extended into the intervertebral disc from the introducer.

The probe may optionally include functional elements which perform different functions, such as transmitting energy and/or material from a location external to the body to a location internal to the disc being accessed upon. Alternatively, material can be transported in the other direction to remove material from the disc, such as removing material by aspiration. The device allows the functional elements to be controllably positioned and manipulated within the guided by manipulation of the handle.

The probe is adapted to slidably advance through the introducer lumen, the probe having a distal section which is extendible through the distal opening at the terminus of the introducer into the disc. Although the length of the distal section can vary with the intended function of the device, as explained in detail below, a typical distance of extension is at least one-half the diameter of the nucleus pulposus, preferably in the range of one-half to one and one-half times the circumference of the nucleus.

In order that the functional elements of the probe can be readily guided to the desired location within a disc, the distal section of the probe is manufactured with sufficient rigidity to avoid collapsing upon itself while being advanced through the nucleus pulposus. The distal section, however, has insufficient rigidity to puncture the annulus fibrosus under the same force used to advance the probe through the nucleus pulposus and around the inner wall of the annulus fibrosus. Absolute penetration ability will vary with sharpness and stiffness of the distal tip of the distal section, but in all cases, a probe of the present invention will advance more readily through the nucleus pulposus than through the annulus fibrosus.

The inability of the distal section of the probe to pierce the annulus can be the result of either the shape of the distal tip of the probe and/or the flexibility of distal portion. The distal tip is considered sufficiently blunt when it does not penetrate the annulus fibrosus but is deflected back into the nucleus pulposus or to the side around the inner wall of the annulus when the distal tip is advanced. Several novel distal tip embodiments are described herein.

2. Design Features of Intervertebral Disc Devices

The devices according to the present invention comprise multiple novel features including, but not being limited to (a) flexible necks adjacent the distal ends of the devices, (b) distal tips which facilitate navigation of the device within an intervertebral disc, (c) attachment mechanisms for the distal tips to the necks, (d) energy delivery mechanisms used with the devices for treating intervertebral discs, and (e) mechanisms for deploying the probe distal end within an intervertebral disc. Each of these different novel features are described herein.

One feature of the probe employed in the device of the present invention is the inability of the distal section of the probe to pierce the annulus. This may be achieved either by the design of the neck of the probe, (i.e., the section of the distal section proximal to the distal tip) or by the design of the distal tip of the probe. The design of the neck and distal tip of the probe can also be utilized to facilitate navigation of the device within the intervertebral disc.

Figure 3A:
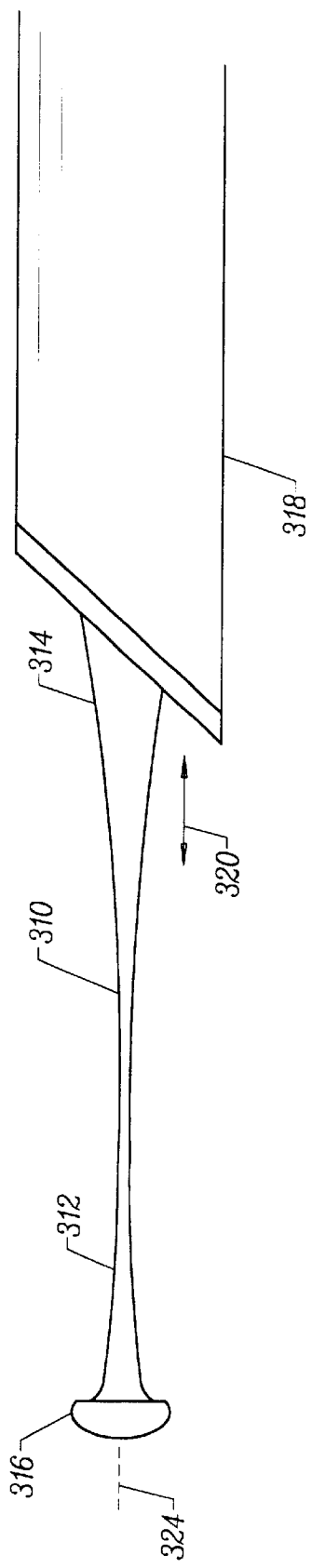
FIG. 3A illustrates a distal section of a probe with a flexible neck and a blunt distal tip.

FIG. 3A shows a distal section 310 of a probe with a flexible neck 312 which tapers from a proximal portion 314 of the distal section. A blunt distal tip 316 is positioned on a distal end of the distal section 310. Also illustrated is the distal end of an introducer 318 from which the probe distal section extends. It is noted that the probe distal section is preferably retractable and extendable 320 relative to the distal end of the introducer.

Figure 3B:
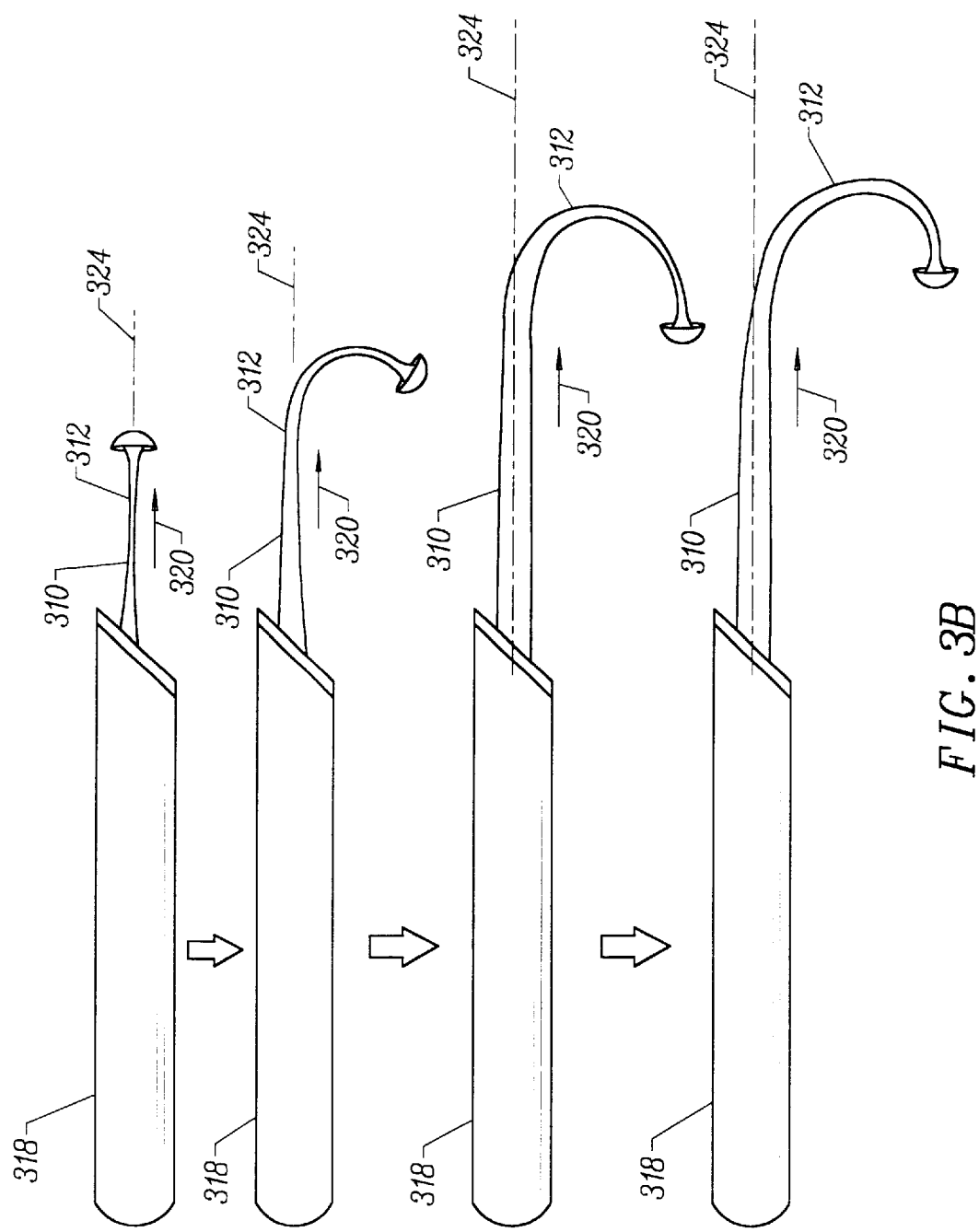
FIG. 3B illustrates a sequence demonstrating the flexing of the flexible neck of the probe.

FIG. 3B illustrates a sequence which shows how the forward advancement of the distal section 310 of a probe from an introducer 318 against tissue causes the probe to bend at the neck 312 relative to the longitudinal axis 324 of the distal section 310. As illustrated in the sequence, further extension 320 of the probe against the tissue causes the distal section 310 of the probe to bend further relative to the longitudinal axis 324 of the distal section 310.

Figure 3C:
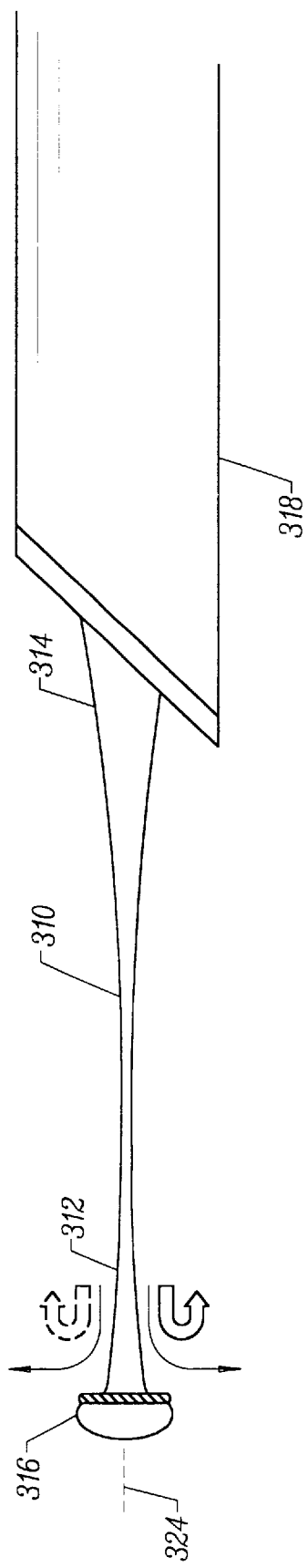
FIG. 3C illustrates a distal section of a probe with a rounded neck.

Rendering the neck flexible can be accomplished by using a series of different neck designs, any of which may be employed in the present invention. For example, FIG. 3C illustrates an embodiment where the neck 312 is rounded. By employing a rounded neck 312, the distal section exhibits no predisposition with regard to the direction in which the neck bends, as indicated by the arrows. Hence, by using a rounded tapered end, bending in any direction relative to the longitudinal axis of the distal section can be achieved.

By contrast, FIG. 3D illustrates a neck 312 which has been flattened on one side 322. Flattening the neck on one side causes the distal section to be predisposed to bending in the plane perpendicular to the flattened surface toward the side of the flattened surface. Hence, by using a neck with a tapered end having one flat surface, the neck is predisposed to bend in a particular direction relative to the longitudinal axis of the distal section.

FIG. 3E illustrates a neck 312 which has been flattened on two opposing sides 324, 326. Flattening the neck on the two opposing sides causes the distal section to be predisposed to bending in planes perpendicular to the two flattened surfaces. If both flattened surfaces are parallel to each other, the neck will preferentially bend in the same plane (as illustrated). If the two flattened surfaces are not parallel to each other, the neck will preferentially bend in the plane perpendicular to the first flattened surface or the plane perpendicular to the second flattened surface.

Figure 3F:
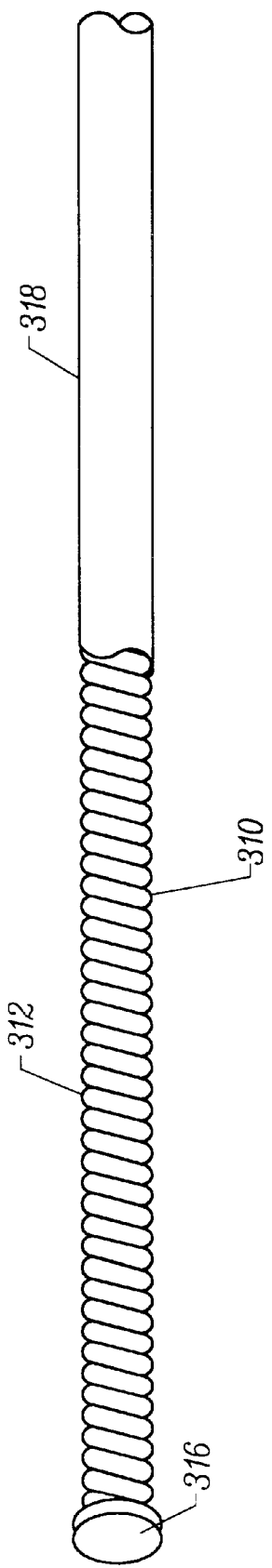
FIG. 3F illustrates a neck where the neck is formed of a coil.

FIG. 3F illustrates a neck 312 where the neck is formed of a coil. The coil neck, like the rounded neck, allows the distal section to bend with no predisposition with regard to which direction the neck bends. Hence, by using a coil neck, bending in any direction relative to the longitudinal axis of the distal section can be achieved.

Figure 4A:
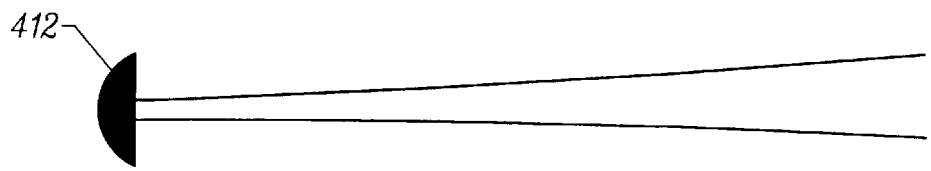
FIGS. 4A–4C illustrate a series of different distal tips which may be attached to the distal sections of the probes employed in the devices of the present invention.
Figure 4B:
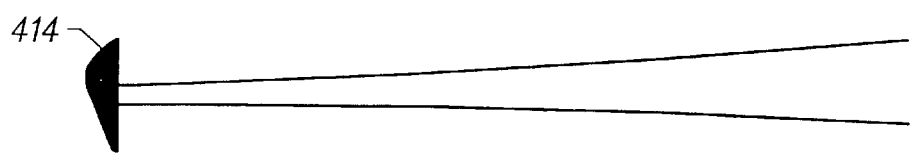
Figure 4C:

FIGS. 4A–4C illustrate a series of different distal tips which may be attached to the distal sections of the probes employed in the devices of the present invention.

FIG. 4A illustrates a dome shaped distal tip 412 where the dome is symmetrical about the longitudinal axis of the distal section of the probe. By having the tip be dome shaped, the tip has less resistance when being pushed through the nucleous pulposus. Meanwhile, by causing the distal tip to be symmetrical, the distal tip does not introduce a predisposition for the distal section to bend in any particular direction.

FIG. 4B illustrates an offset dome shaped distal tip 414 where the dome is asymmetrical about the longitudinal axis of the distal section of the probe. By causing the distal tip to be asymmetrical, the distal tip introduces a predisposition for the distal section to bend on the side of the tip where the tip is larger.

FIG. 4C illustrates a flat distal tip 416. By causing the distal tip to be flat, the resistance felt by the distal tip when pushed through the nucleous pulposus is enhanced. Optionally, although not shown, a predisposition for the distal section to bend in a particular direction can be imparted by designing the distal tip to be asymmetrical relative to the longitudinal axis of the distal section.

Figure 5A:
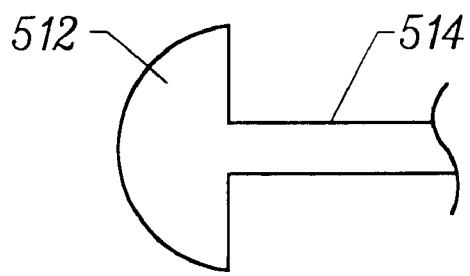
FIGS. 5A–5C illustrate a series of different distal tip attachment mechanisms which may be used to attach a distal tip to a distal section of a probe employed in the devices of the present invention.
Figure 5B:
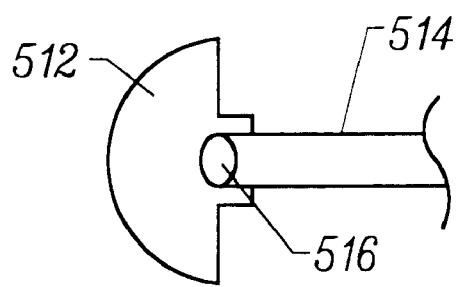
Figure 5C:
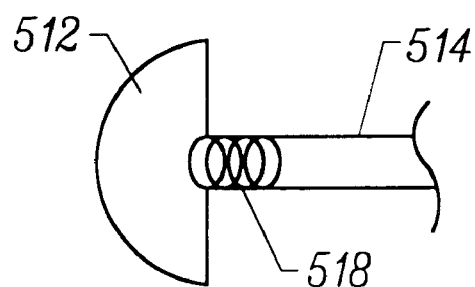

FIGS. 5A–5C illustrate a series of different distal tip attachment mechanisms which may be used to attach a distal tip to a distal section of a probe employed in the devices of the present invention. Each of these different distal tip attachment mechanisms causes the distal tip and the distal section of the probe to move through the dense colloidal material of the nucleous pulposus.

FIG. 5A illustrates an embodiment where the distal tip 512 and the neck 514 of the distal section is one unit made of the same material. In this embodiment, the distal tip is rigid relative to the neck 514 of the distal section.

FIG. 5B illustrates an embodiment where the distal tip 512 and the neck 514 of the distal section are attached by a pivot mechanism 516, such as a ball and socket mechanism, which allows the orientation of the distal tip to rotate relative to the neck 514.

FIG. 5C illustrates an embodiment where the distal tip 512 and the neck 514 of the distal section are attached by a spring 518. A spring mechanism 518 not only allows the distal tip 512 to rotate relative to the neck 514, the spring mechanism also allows the distal tip to be distended away from the neck 514.

It is noted with regard to the neck, distal tip and attachment mechanisms that any combination of the three may be used since it is anticipated that one may wish to alter the navigation behavior of the probe within the nucleous pulposus by manipulating these three variables.

Figure 6:
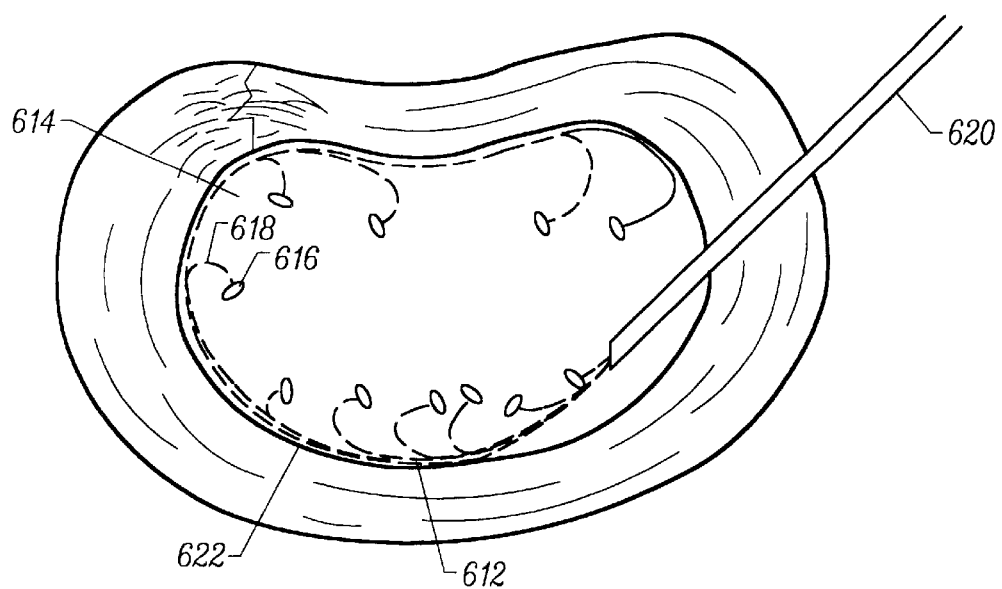
FIG. 6 illustrates movement with bending of a distal section within nucleous pulposus as the distal section of the device is advanced within the intervertebral disc.

FIG. 6 illustrates movement with bending of a distal section 612 within nucleous pulposus 614 as the probe distal section is advanced within the intervertebral disc. Note that the introducer 620 remains stationary as the probe is advanced. As can be seen, as the distal section 612 is advanced, the distal tip 616 and neck 618 are bent away from the intervertebral wall 622. This may be accomplished either by predisposing the tip and/or neck to bending in a particular direction. It may also be accomplished by the wall itself having a certain curvature. As the probe distal section is advanced, the distal section bends until the tension created by the bending exceeds the force that is being applied to the distal section by the tissue to cause the bending. Hence, the rigidity of the flexible distal section limits the amount that the distal section ultimately bends.

FIGS. 7A–7C illustrate a sequence which shows how tissue force resisting the forward advancement of the probe within the intervertebral disc causes the distal section of the probe to bend. FIG. 7A shows a probe 710 with an asymmetrical distal tip 712. As illustrated, the asymmetry of the tip causes more resistance to be applied to the larger side of the asymmetrical distal tip 712. As illustrated in FIG. 7B, the asymmetrical resistance causes the distal section of the probe to bend. As the distal section is advanced further, force begins to be applied to the back of the distal tip, causing the distal section to bend further. As the distal section is advanced further, more force is applied to the distal tip 712, as shown by the arrows in FIG. 7C against the distal tip 712.

Figure 8I:
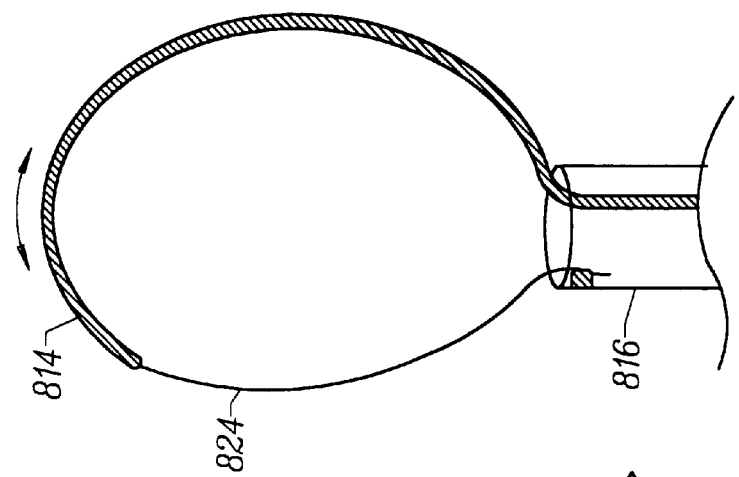
FIG. 8I illustrates that the probe shown in FIG. 8G may be extended along the guide wire out of the distal end of the introducer.
Figure 8H:
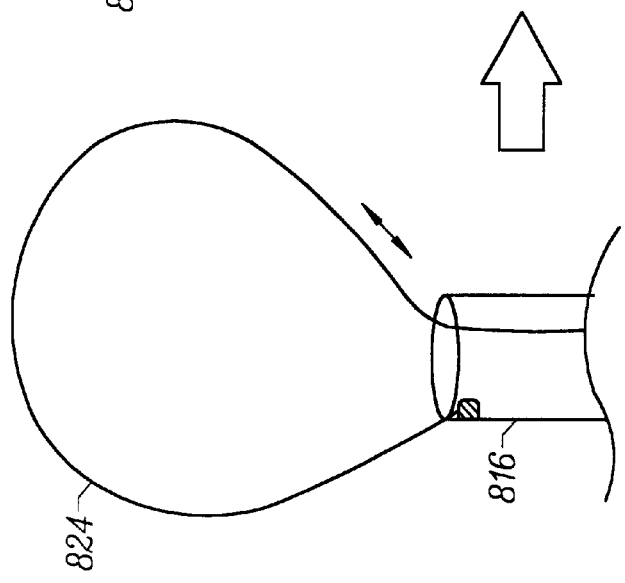
FIGS. 8A–8Q illustrate a series of different embodiments for deploying the distal section of the probe from the introducer so that the probe approaches the internal wall of the annulus fibrosus.
FIG. 8B illustrates that the probe shown in FIG. 8A may be extended out of the distal end of the introducer to cause the probe to form a loop.
FIG. 8C illustrates another embodiment where the distal end of the probe is attached to the distal end of the introducer via a guide wire lead.
FIG. 8D illustrates that the probe shown in FIG. 8C may be extended out of the distal end of the introducer to cause the probe to form a loop.
FIG. 8E illustrates another embodiment where the distal end of the probe forms a loop within the introducer where both sides of the probe are separately extendable and retractable relative to the distal end of the introducer.
FIG. 8F illustrates that the probe shown in FIG. 8E may be extended out of the distal end of the introducer to cause the probe to form a loop.
FIG. 8G illustrates another embodiment where a guide wire is attached to the distal end of the introducer.
FIG. 8J illustrates another embodiment where a guide wire forms a loop within the introducer where both sides of the guide wire loop are separately extendable and retractable relative to the distal end of the introducer.
FIG. 8K illustrates that extension of the guide wire shown in FIG. 8J out of the distal end of the introducer causes the guide wire to form a loop.
FIG. 8L illustrates that a probe may be extended along the guide wire shown in FIG. 8K out of the distal end of the introducer.
FIGS. 8M–8O illustrate another embodiment of the embodiment shown in FIG. 8J where the guide wire is capable of being folded upon itself.
FIG. 8P provides a sequence illustrating the deployment of the guide wire from an introducer within a disc such that the guide wire encircles the internal wall of the disc.

Referring back to FIG. 1E, the longitudinal axis of the introducer 169 causes an element extended from the introducer 169 to have a trajectory toward the center of the disc. However, it is desirable to be able to deploy the probe and any functional elements on the probe adjacent the internal wall 22 of the annulus fibrosus. FIGS. 8A–8Q illustrate a series of different embodiments for deploying the distal section of the probe from the introducer so that the probe approaches the internal wall of the annulus fibrosus.

FIG. 8A illustrates an embodiment where the distal end 812 of the probe 814 is attached to the distal end of the introducer 816. As illustrated in FIG. 8B, extension of the distal end 812 of the probe 814 out of the distal end of the introducer 816 in this embodiment (denoted by the arrow) causes the probe to form a loop. Broadening of the loop by further extension of the probe causes the probe to encircle the internal wall 22 of the annulus fibrosus.

FIG. 8C illustrates another embodiment where the distal end 812 of the probe 814 is attached to the distal end of the introducer 816 via a guide wire lead 818. The guide wire lead 818 is thinner than the probe 814 and thus can adopt a smaller radius of curvature than the probe 814. This allows a smaller bore introducer 816 to be utilized or a larger probe 814 to be utilized since both the distal end of the probe and the guide wire lead can be more readily accommodated within the introducer. As illustrated in FIG. 8D, extension of the distal end 812 of the probe 814 out of the distal end of the introducer 816 in this embodiment (denoted by the arrow) causes the probe to form a loop. Broadening of the loop by further extension of the probe causes the probe to encircle the internal wall of the annulus fibrosus.

FIG. 8E illustrates another embodiment where the distal end of the probe 814 forms a loop within the introducer where both sides of the probe 814 are separately extendable and retractable relative to the distal end of the introducer 816. As illustrated in FIG. 8F, extension of the probe 814 out of the distal end of the introducer 816 in this embodiment (denoted by the arrow) causes the probe to form a loop. Shown as boxes on the probe are a series of electrodes 820 for delivering energy to tissue within the disc. It is noted that other functional elements can also be positioned on the probe. Broadening of the loop by further extension of the probe causes the probe to encircle the internal wall of the annulus fibrosus. Extending or retracting one side of the loop shaped probe causes the electrodes to move relative to the inner wall.

Figure 8G:
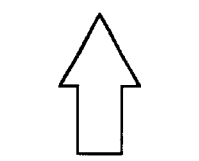

FIG. 8G illustrates another embodiment where a guide wire 824 is attached to the distal end of the introducer 816. The guide wire 824 is thinner than the probe 814 and thus can adopt a smaller radius of curvature than the probe 814. This allows a smaller bore introducer 816 to be utilized or a larger probe 814 to be utilized since both the distal end of the probe and the guide wire lead can be more readily accommodated within the introducer. As illustrated in FIG. 8H, extension of the guide wire 824 out of the distal end of the introducer 816 in this embodiment (denoted by the arrow) causes the guide wire 824 to form a loop. Broadening of the loop by further extension of the guide wire 824 causes the guide wire 824 to encircle the internal wall of the annulus fibrosus. As illustrated in FIG. 8I, a probe 814 may be extended along the guide wire 824 out of the distal end of the introducer. The probe 814 may include different functional elements for treating tissue within the disc.

FIG. 8J illustrates another embodiment where a guide wire 824 forms a loop within the introducer where both sides of the guide wire loop 824 are separately extendable and retractable relative to the distal end of the introducer 816. The guide wire 824 is thinner than the probe 814 and thus can adopt a smaller radius of curvature than the probe 814. This allows a smaller bore introducer 816 to be utilized or a larger probe 814 to be utilized since both the distal end of the probe and the guide wire lead can be more readily accommodated within the introducer. As illustrated in FIG. 8K, extension of the guide wire 824 out of the distal end of the introducer 816 in this embodiment (denoted by the arrows) causes the guide wire 824 to form a loop. Broadening of the loop by further extension of the guide wire 824 causes the guide wire 824 to encircle the internal wall of the annulus fibrosus. As illustrated in FIG. 8L, a probe 814 may be extended along the guide wire 824 out of the distal end of the introducer. The probe 814 may include different functional elements for treating tissue within the disc.

FIGS. 8M–8O illustrate another embodiment of the embodiment shown in FIG. 8J where the guide wire 824 is capable of being folded upon itself. FIG. 8M illustrates the guide wire unfolded where section I includes a guide wire with a thin, concave shape, section II includes a tapered section that provides an area where the guide wire is folded upon itself, and section III includes a rounded section such that the rounded section fits within the concave shape of section I. FIG. 8N shows the cross sections of guide wire sections I–III illustrated in FIG. 8M. As illustrated in FIG. 8O, the guide wire may be folded upon itself where the crease is at section II, and section I and section III come together. By having sections I and III fit together, the folded guide wire can more readily be accommodated within an introducer.

Figure 8P:
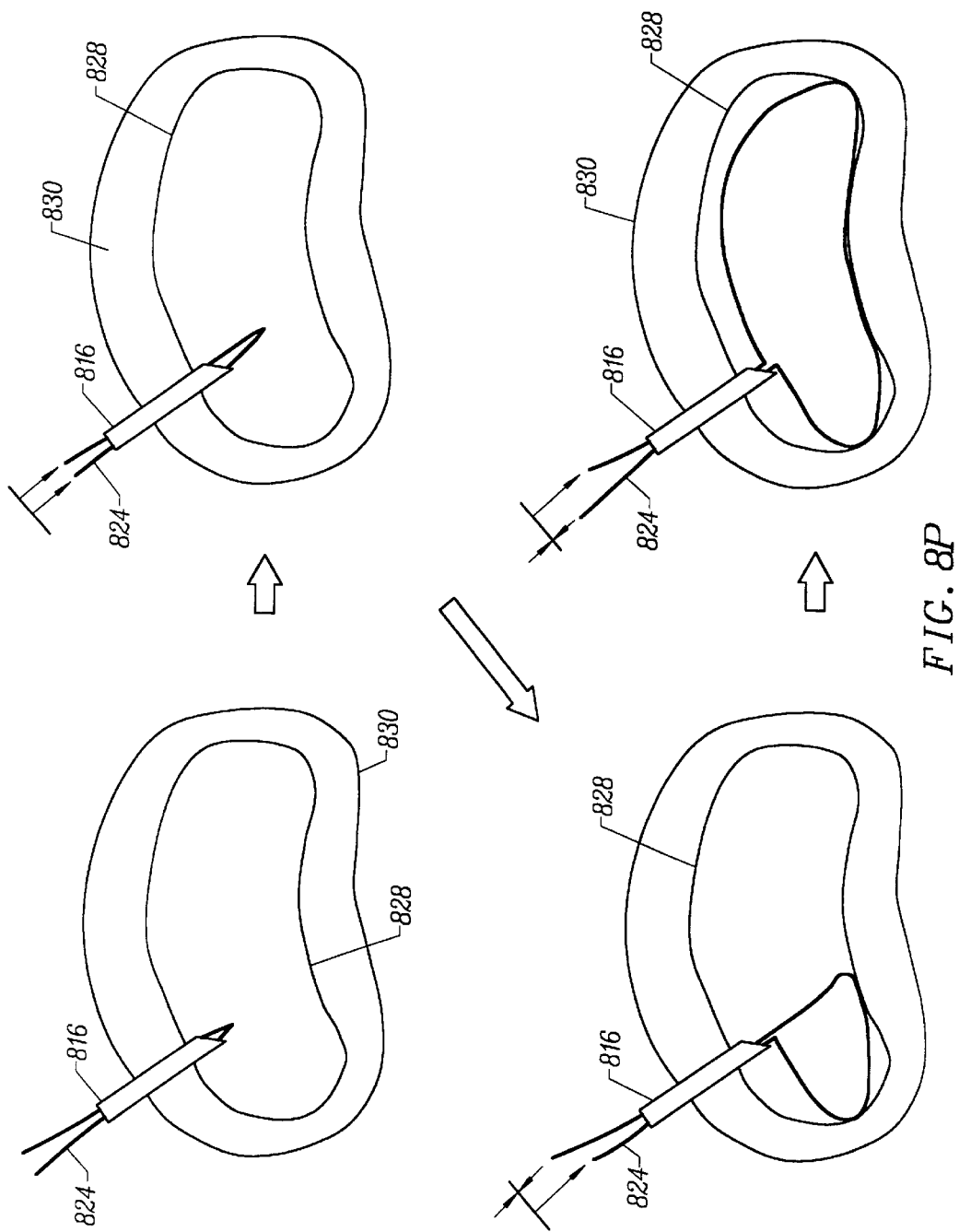
Figure 8Q:
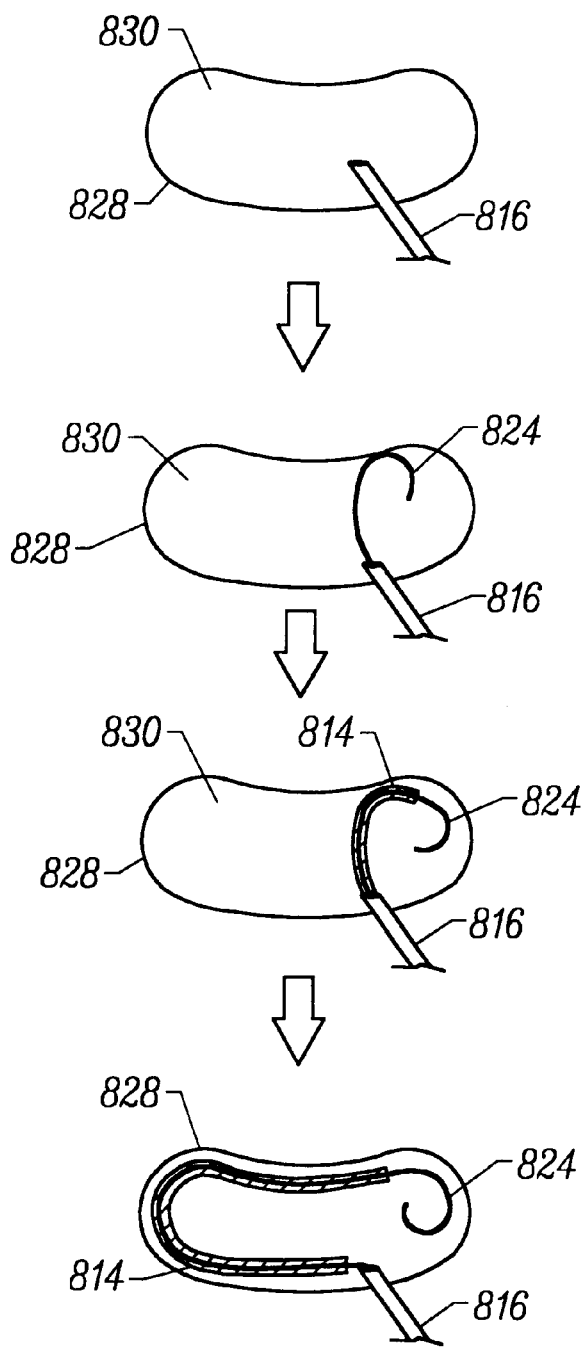

FIG. 8P provides a sequence illustrating the deployment of the guide wire 824 from an introducer 816 within a disc such that the guide wire 824 encircles the internal wall 828 of the disc 830. As illustrated in the sequence, the crease allows the guide wire loop to be more tightly folded together. By then extending one side of the looped guide wire, a side of the guide wire can be expanded. Then, the other side of the guide wire loop may be expanded. The way in which sections I and III fit together allow for the different sides of the loop to be separately moved relative to each other and extended and retracted from the introducer.

It is noted that although FIGS. 8M–8P are described with regard to guide wires, that the probe may also be designed with a crease so that it may be deployed in a similar manner as shown in FIGS. 8E, 8F and then in FIG. 8P.

FIG. 8Q illustrates yet another embodiment where a guide wire 824 and probe 814 are used in combination to deploy the probe 814 adjacent an internal wall 828 of a disc 830. As illustrated, an introducer 816 is introduced into the disc. A guide wire 824 is then extended from the introducer 816. The guide wire is predisposed to forming a loop when extended from the introducer 816 and thus moves toward one side of the disc. A probe 814 is then extended in combination with the guide wire from the introducer 816. The looped distal end of the guide wire 824 serves to immobilize the distal end of the guide wire. This then allows the probe 814 to be expanded, thereby causing the probe to move along the wall of the disc.

It is noted with regard to the above embodiments that the distal portion of the probe and/or the guide wire may be pre-bent, if desired. "Pre-bent" or "biased" means that a portion of the probe, guide wire, or other structural element under discussion, is made of a spring-like material that is bent in the absence of external stress but which, under selected stress conditions (for example, while the probe is inside the introducer), is linear. The un-stressed wire loop diameter preferably has a diameter between about 0.025–1 inch, more preferably between about 0.05–0.75 inch, or most preferably between about 0.1–0.5 inch. The diameter of the guide wire preferably has a diameter between about 0.005–0.05 inch, more preferably between about 0.007–0.035 inch, or most preferably between about 0.009–0.025 inch. Such a biased distal portion can be manufactured from either spring metal or super elastic memory material (such as Tinel.RTM. nickel-titanium alloy, Raychem Corp., Menlo Park Calif.). The introducer (at least in the case of a spring-like material for forming the probe) is sufficiently strong to resist the bending action of the bent distal end and maintain the biased distal portion in alignment as it passes through the introducer. Compared to unbiased probes, a probe or guide wire with a biased distal portion encourages advancement of the probe or guide wire substantially in the direction of the bend relative to other lateral directions. Biasing the probe or guide wire distal end also further decreases likelihood that the distal end of the probe or guide wire will be forced through the annulus fibrosus under the pressure used to advance the probe.

In addition to biasing the distal section of the probe or guide wire prior to insertion into an introducer, the distal section of the probe or guide wire can be provided with a mechanical mechanism for deflecting the distal section, such as a wire that deflects the distal section in the desired direction upon application of force to the proximal end of the deflection wire. Any device in which bending of the distal end of a probe or guide wire is controlled by the physician is "actively settable." In addition to a distal section that is actively settable by action of a wire, other methods of providing a bending force at the distal section can be used, such as hydraulic pressure and electromagnetic force (such as heating a shaped memory alloy to cause it to contract). Any of a number of techniques can be used to provide selective bending of the probe in one lateral direction.

Optionally a sheath may be employed in combination with the probe (or guide wire) to facilitate directing movement of the probe within a disc. The sheath can be made of a variety of different materials including but not limited to polyester, rayon, polyamide, polyurethane, polyethylene, polyamide and silicone.

FIGS. 9A–9C illustrate one embodiment where a sheath having a predefined curvature adjacent its distal end introduces curvature to a guide wire or probe extended from the sheath. FIG. 9A illustrates the distal end of an introducer 912 with a sheath 914 and a probe 916 extending from the introducer 912. It is noted that a guide wire could be used in place of the probe 916, the probe being later drawn over the extended guide wire.

FIG. 9B illustrates sheath 914 being extended from the distal end of the introducer 912. As can be seen, the sheath 914 has a predefined curvature 918 adjacent its distal end. This curvature causes the probe 916 (or guide wire) to likewise be curved. As illustrated in FIG. 9C, the sheath 914 is only extended a limited distance. Meanwhile, the probe is further extendible relative to the sheath 914. This allows a degree of curvature to be maintained by the sheath at a known, preselected distance that is distal relative to the introducer. Meanwhile, the probe 916 can be extended further out of the sheath. The probe itself may optionally have its own preselected degrees of curvature.

Since the purpose of the devices of the present invention is to treat tissue within an intervertebral disc by operation of the device adjacent to or inside the disc, one or more functional elements may be provided in or on the distal section of the probe to carry out that purpose.

Non-limiting examples of functional elements include any element capable of aiding diagnosis, delivering energy, or delivering or removing a material from a location adjacent the element's location in or on the probe, such as an opening in the probe for delivery of a fluid (e.g., dissolved collagen to seal the fissure) or for suction, a thermal energy delivery device (heat source), a mechanical grasping tool for removing or depositing a solid, a cutting tool (which includes all similar operations, such as puncturing), a sensor for measurement of a function (such as electrical resistance, temperature, or mechanical strength), or a functional element having a combination of these functions.

The functional element can be at varied locations on the distal section of the probe, depending on its intended use. Multiple functional elements can be present, such as multiple functional elements of different types (e.g., a heat source and a temperature sensor) or multiple functional elements of the same type (e.g., multiple heat sources spaced along the intradiscal portion).

One of the possible functional elements present on the distal section of the probe is a thermal energy delivery device. A variety of different types of thermal energy can be delivered including but not limited to resistive heat, radiofrequency (RF), coherent and incoherent light, microwave, ultrasound and liquid thermal jet energies. In these embodiments, the electrode array length is preferably 0.2–5 inches long, more preferably 0.4–4 inches long, and most preferably 0.5–3 inches long.

Some embodiments of the device have an interior infusion lumen. Infusion lumen is configured to transport a variety of different media including but not limited to electrolytic solutions (such as normal saline), contrast media (such as Conray meglumine iothalamate), pharmaceutical agents, disinfectants, filling or binding materials such as collagens or cements, chemonucleolytic agents, and the like, from a reservoir exterior to the patient to a desired location within the interior of a disc (i.e., the fissure). Further, the infusion lumen can be used as an aspiration lumen to remove nucleus material or excess liquid or gas (naturally present, present as the result of a liquefying operation, or present because of prior introduction) from the interior of a disc. When used to transport a fluid for irrigation of the location within the disc, the infusion lumen is sometimes referred to as an irrigation lumen. Infusion lumen can be coupled to medium reservoir through the probe.

Optionally, one or more sensor lumens may be included. An example of a sensor lumen is a wire connecting a thermal sensor at a distal portion of the probe to control elements attached to a connector in the proximal handle of the probe.

Energy directing devices may also optionally be included, such as thermal reflectors, optical reflectors, thermal insulators, and electrical insulators. An energy directing device may be used to limit thermal and/or electromagnetic energy delivery to a selected site of the disc and to leave other sections of the disc substantially unaffected. An energy directing device can be positioned on an exterior surface of the distal section of the probe, as well as in an internal portion of the probe. For example, energy can be directed to the walls of a fissure to cauterize granulation tissue and to shrink the collagen component of the annulus, while the nucleus is shielded from excess heat.

Therapeutic and/or diagnostic agents may be delivered within the disc via the probe. Examples of agents that may be delivered include, but are not limited to, electromagnetic energy, electrolytic solutions, contrast media, pharmaceutical agents, disinfectants, collagens, cements, chemonucleolytic agents and thermal energy.

In one embodiment, the device includes markings which indicate to the physician how far the probe has been advanced into the nucleus. Such a visible marking can be positioned on the handle or on the flexible tubing. Preferred are visible markings every centimeter to aid the physician in estimating the probe tip advancement.

If desired, visible markings can also be used to show twisting motions of the probe to indicate the orientation of the bending plane of the distal portion of the probe. It is preferred, however, to indicate the distal bending plane by the shape and feel of the proximal end of the probe assembly. The probe can be attached to or shaped into a handle that fits the hand of the physician and also indicates the orientation of the distal bending plane. Both the markings and the handle shape thus act as control elements to provide control over the orientation of the bending plane; other control elements, such as plungers or buttons that act on mechanical, hydrostatic, electrical, or other types of controls, can be present in more complex embodiments of the invention.

Additionally, a radiographically opaque marking device can be included in the distal portion of the probe (such as in the tip or at spaced locations throughout the intradiscal portion) so that advancement and positioning of the intradiscal section can be directly observed by radiographic imaging. Such radiographically opaque markings are preferred when the intradiscal section is not clearly visible by radiographic imaging, such as when the majority of the probe is made of plastic instead of metal. A radiographically opaque marking can be any of the known (or newly discovered) materials or devices with significant opacity. Examples include but are not limited to a steel mandrel sufficiently thick to be visible on fluoroscopy, a tantalum/polyurethane tip, a gold-plated tip, bands of platinum, stainless steel or gold, soldered spots of gold and polymeric materials with radiographically opaque filler such as barium-sulfate. A resistive heating element or an Rf electrode(s) may provide sufficient radio-opacity in some embodiments to serve as a marking device.

Figure 10A:
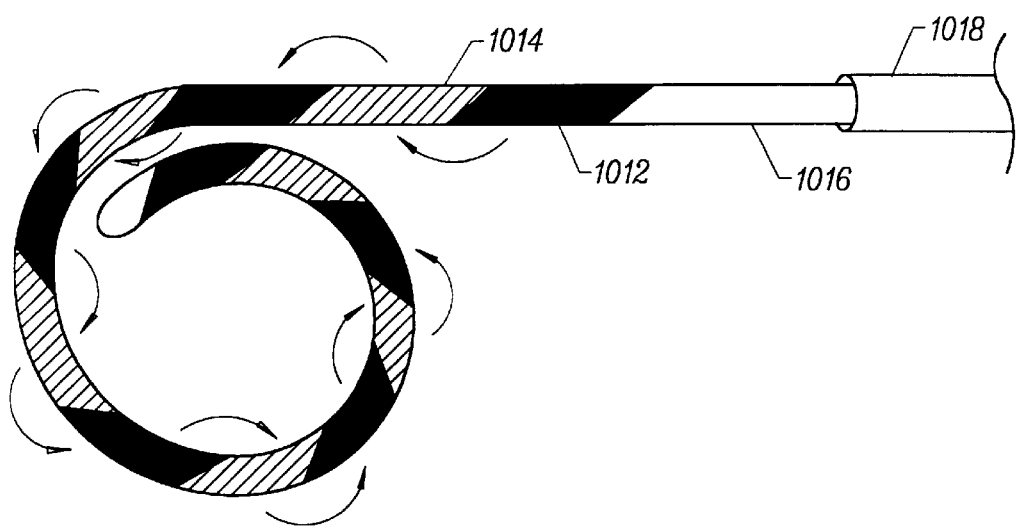
FIGS. 10A–10C illustrate a series of preferred designs for thermal energy delivery devices which may be used in combination with the devices of the present invention.
Figure 10B:
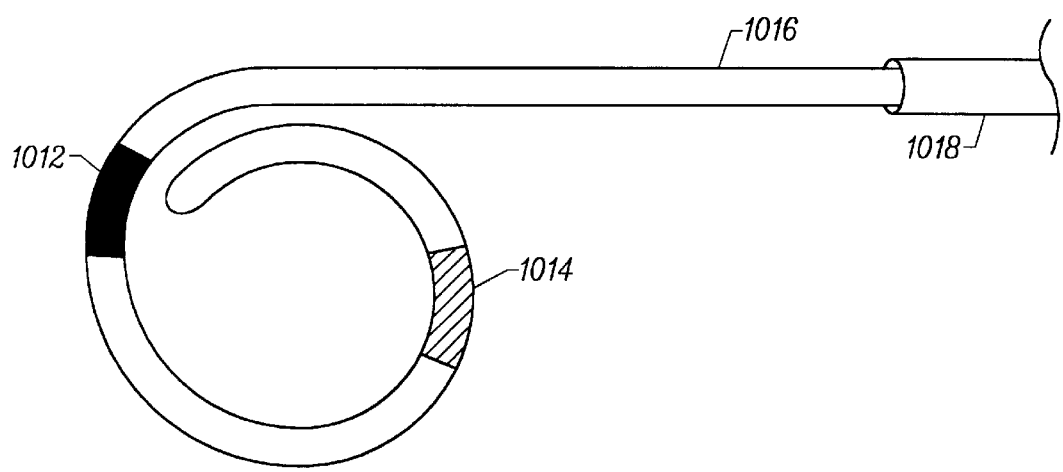
Figure 10C:
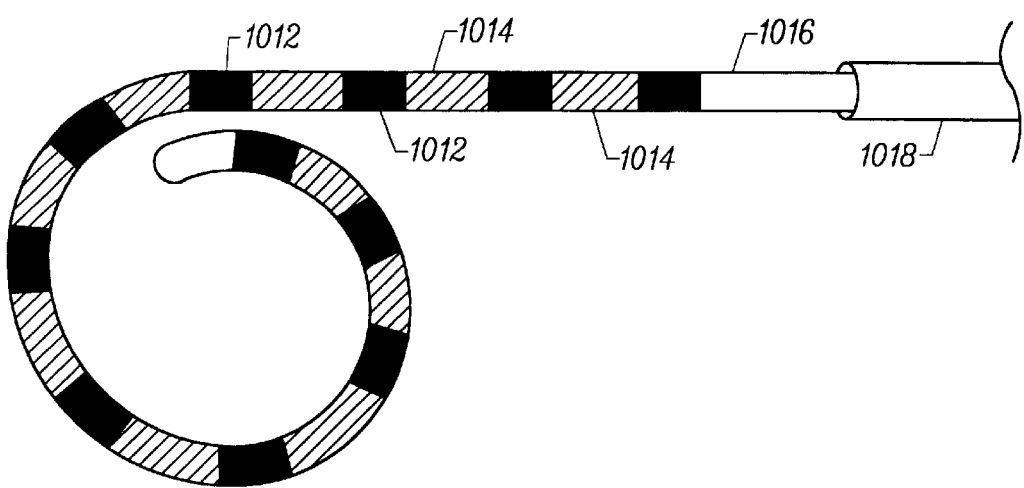

FIGS. 10A–10C illustrate a series of preferred designs for bipolar thermal energy delivery devices which may be used in combination with the devices of the present invention. It is noted that radio frequency energy or resistive heating may be performed using these designs.

FIG. 10A illustrates an embodiment where the thermal energy delivery device is a bipolar electrode comprising an active electrode 1012 and a return electrode 1014 where the active electrode 1012 and return electrode 1014 are each spirally wrapped around a portion of the distal section of the probe 1016. The probe is shown to be extending from an introducer 1018. When a potential is introduced between the active electrode 1012 and return electrode 1014, current flows through the tissue adjacent the two electrodes. Since the two electrodes are wrapped in a spiral about the active electrode, energy transfer is distributed along the length of the probe, thereby more evenly heating the adjacent tissue.

It is noted that the distal section of the probe 1016 shown in FIG. 10A is predisposed to form a loop. By sizing the loop to approximate the inner diameter of an intervertebral disc, it is possible to cause the loop shaped probe to abut the internal wall of the disc. Then, by applying a potential between the electrodes, energy can be somewhat uniformly delivered to tissue adjacent the internal wall of the disc. It is noted that over time, tissue interior to the loop may also be uniformly treated by the loop shaped electrode.

FIG. 10B illustrates another embodiment of a thermal energy delivery device. Like the embodiment shown in FIG. 10A, the distal section of the probe 1016 is predisposed to form a loop. By sizing the loop to approximate the inner diameter of an intervertebral disc, it is possible to cause the loop shaped probe to abut the internal wall of the disc. As illustrated in FIG. 10B, an active electrode 1012 and a return electrode 1014 are positioned on opposing sides of the loop. By applying a potential between the electrodes, energy can be delivered to tissue positioned between the two electrodes.

FIG. 10C illustrates another embodiment of a thermal energy delivery device. Like the embodiment shown in FIGS. 10A and 10B, the distal section of the probe 1016 is predisposed to form a loop. As illustrated, a series of alternating active 1012 and return 1014 electrodes are positioned along the distal section of the probe. By applying a potential between the series of active and return electrodes, energy can be delivered to tissue along the length of the probe.

Figure 11A:
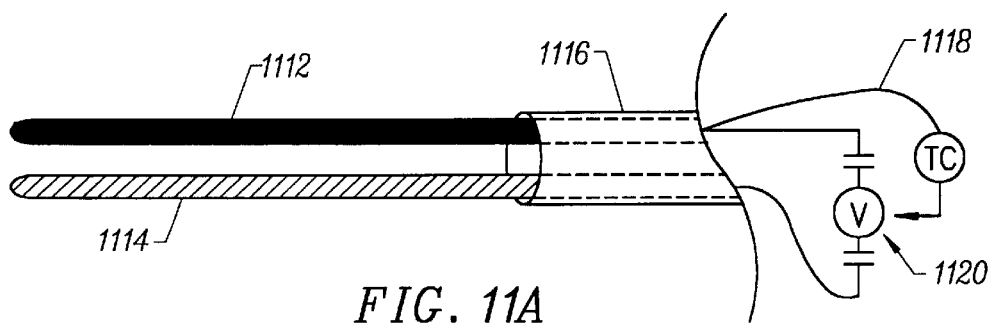
FIGS. 11A and 11B illustrate yet another embodiment for a thermal energy delivery device which may be used in combination with the devices of the present invention.
Figure 11B:
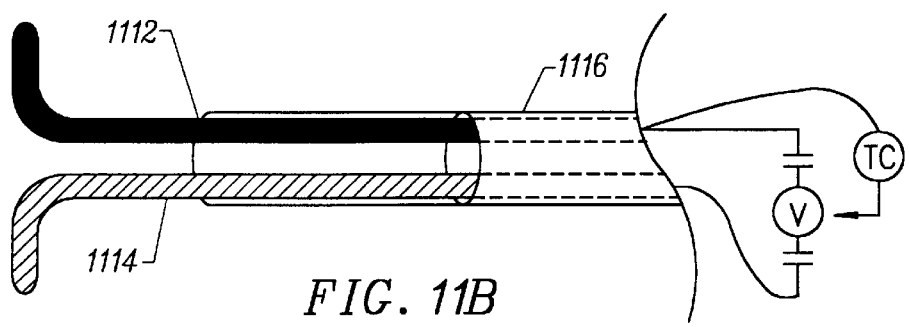

FIGS. 11A and 11B illustrate yet another embodiment for a thermal energy delivery device which may be used in combination with the devices of the present invention. It is noted that radio frequency energy or resistive heating may be performed using these designs.

FIG. 11A illustrates an embodiment where a pair of probes which form an active electrode 1112 and a return electrode 1114 extend from an introducer or sheath 1116 and are spaced apart from each other. By applying a potential between the active and return electrodes, energy can be delivered to tissue along the length of the probes.

FIG. 11B illustrates a variation on the embodiment shown in FIG. 11A where the pair of probes which form an active electrode 1112 and a return electrode 1114 diverge from each other adjacent their distal ends. By applying a potential between the active and return electrodes, energy can be delivered to tissue along the length of the probes. By having the two probes diverge, a larger area of tissue may be treated.

Also shown in FIGS. 11A and 11B is a thermocouple 1118 for sensing temperature and a feedback loop 1120 for regulating the potential between the electrodes in response to measurements by the thermocouple.

It is noted that other energy delivery devices may also be used with the intervertebral disc treatment devices of the present invention beyond those described with regard to FIGS. 10A–C and 11A–B, including those described in U.S. Pat. Nos. 6,135,999; 6,126,682; 6,122,549; 6,099,514; 6,095,149; 6,073,051; 6,007,570; 5,980,504, which are each incorporated herein by reference.

When the device is used as a resistive heating device, the amount of thermal energy delivered to the tissue is a function of (i) the amount of current passing through heating element, (ii) the length, shape, and/or size of heating element, (iii) the resistive properties of heating element, (iv) the gauge of heating element, and (v) the use of cooling fluid to control temperature. All of these factors can be varied individually or in combination to provide the desired level of heat. Power supply associated with heating element may be battery based. The probe can be sterilized and may be disposable.

In some embodiments, thermal energy is delivered to a selected section of the disc in an amount that does not create a destructive lesion to the disc, other than at most a change in the water content of the nucleus pulposus. In one embodiment there is no removal and/or vaporization of disc material positioned adjacent to an energy delivery device positioned in a nucleus pulposus. Sufficient thermal energy is delivered to the disc to change its biochemical and/or biomechanical properties without structural degradation of tissue.

Thermal energy may be used to cauterize granulation tissue which is pain sensitive and forms in a long-standing tear or fissure. Additionally or alternatively, thermal energy is used to seal at least a part of the fissure. To do that, the disc material adjacent to the fissure is typically heated to a temperature in the range of 45–70 degree C. which is sufficient to shrink and weld collagen. In one method, tissue is heated to a temperature of at least 50 degree C. for times of approximately one, two, three minutes, or longer, as needed to shrink the tissue back into place.

Delivery of thermal energy to the nucleus pulposus removes some water and permits the nucleus pulposus to shrink. This reduces a "pushing out" effect that may have contributed to the fissure. Reducing the pressure in the disc and repairing the fissure may help stabilize the spine and reduce pain.

Global heating of the disc also can be used to cauterize the granulation tissue and seal the fissure. In this embodiment of the method, the heating element is positioned away from the annulus but energy radiates to the annulus to raise the temperature of the tissue around the fissure. This global heating method can help seal a large area or multiple fissures simultaneously.

Figure 12:
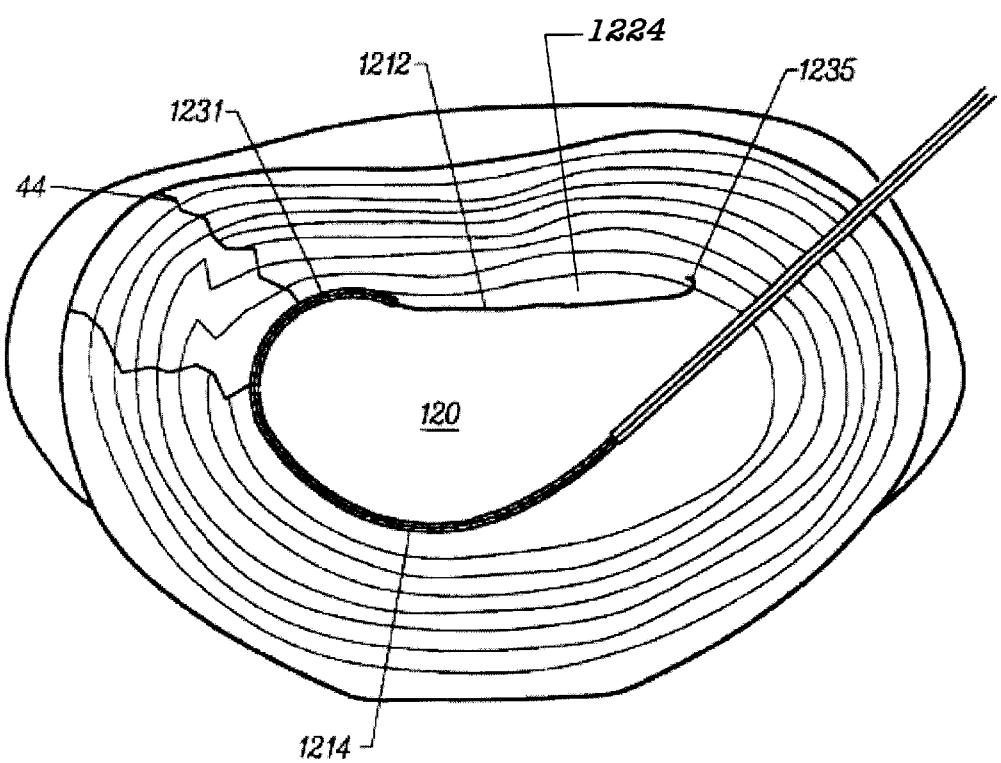
FIG. 12 shows an embodiment of the guide wire with an attachment mechanism at the distal tip for attaching the guide wire to the inner wall of the intervertebral disc.

FIG. 12 shows an embodiment of the guide wire 1224 with a mechanism 1235 at the end of the distal portion 1212 of the guide wire for attaching the guide wire to the inner wall of the intervertebral disc. By attaching the attachment mechanism to the inner wall, displacement of the guide wire is prevented during subsequent exchange and withdrawal of other system components. The guide wire 1224 is extended into the intervertebral disc and navigated to a desired portion along the inner wall of the disc. The attachment mechanism is inserted and held in place such that the distal portion 1212 is attached to the inner wall tissue. As illustrated in FIG. 12, extension of the probe 1214 over the guide wire into the nucleus 120 of the intervertebral disc causes the probe to move along the path of the guide wire. The attachment of the guide wire to the inner wall assists in keeping the guide wire in place despite force on the guide wire by the probe. In the instance illustrated, the distal portion 1231 of the probe 1214 is positioned at an annular fissure 44 for performing a function as described herein. All publications and patent applications mentioned in this specification are herein incorporated by reference to the same extent as if each individual publication or patent application was specifically and individually indicated to be incorporated by reference.

While the present invention is disclosed with reference to preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims. Any patents, papers, and books cited in this application are to be incorporated herein in their entirety.

We claim:

1. An intervertebral disc device comprising:
    a probe capable of being extended from a distal end of an introducer that is percutaneously delivered into an interior of an intervertebral disc, the probe forming a loop when extended from the distal end of the introducer, the loop having first and second proximal ends external to the introducer which are brought together adjacent the introducer distal end to form the loop by the proximal ends being either attached to or entering the distal end of the introducer, the first and second proximal ends of the probe having different cross sectional geometries; and
    a proximal handle for externally causing the probe to be extended from the distal end of the introducer and externally guiding the probe within an intervertebral disc.

2. An intervertebral disc device according to claim 1 wherein the device further includes an introducer, the first proximal end of the probe being attached to the introducer adjacent a distal end of the introducer, the second proximal end of the probe being extendable from the introducer distal end to form the loop.

3. An intervertebral disc device according to claim 2 wherein the first proximal end of the probe is attached to the introducer adjacent the distal end of the introducer by a guide wire lead.

4. An intervertebral disc device according to claim 1 wherein the first and second proximal ends of the probe are each separately extendable from the introducer distal end to form the loop.

5. An intervertebral disc device according to claim 1 wherein the different cross sectional geometries of the first and second proximal ends are selected such that the cross sectional geometry of the first proximal end is a compliment of the cross sectional geometry of the second proximal end.

6. An intervertebral disc device according to claim 5 wherein:

the first proximal end has round cross section, the second proximal end has a thin, concave cross section and a concave side, and the first proximal end can be folded into the concave side.

7. An intervertebral disc device according to claim 1 wherein the device further includes flexible tubing disposed between the proximal handle and the introducer.

8. An intervertebral disc device according to claim 1 wherein the probe further includes an electromagnetic energy device capable of supplying energy within the intervertebral disc.

9. An intervertebral disc device according to claim 8 wherein the electromagnetic energy device is capable of delivering energy selected from a group consisting of coherent light, incoherent light, radiofrequency ("RF") waves, microwaves, and ultrasound waves.

10. An intervertebral disc device according to claim 8 wherein the electromagnetic energy device comprises electrodes adapted to deliver RF energy.

11. An intervertebral disc device according to claim 10 wherein the RF electrodes have a monopolar configuration.

12. An intervertebral disc device according to claim 10 wherein the RF electrodes have a bipolar configuration.

13. An intervertebral disc device according to claim 8 wherein the electromagnetic energy device comprises a resistive heating mechanism.

14. An intervertebral disc device according to claim 1 wherein the handle further comprises a probe control element for controlling the movement of the probe adjacent a distal end of the device.

15. An intervertebral disc device according to claim 1 wherein the probe further includes a functional element which performs a function selected from the group consisting of transmitting energy to tissue within an intervertebral disc, delivering material to within an intervertebral disc, and removing material within an intervertebral disc.

16. An intervertebral disc device according to claim 1 wherein the first proximal end has a round cross section and the second proximal end has a thin, concave cross section and a concave side.

17. An intervertebral disc device comprising:
a guide wire capable of being extended from a distal end of an introducer that is percutaneously delivered into an interior of an intervertebral disc, the guide wire forming a loop when extended from the distal end of the introducer, the loop having first and second proximal ends external to the introducer which are brought together adjacent the introducer distal end to form the loop by the proximal ends being either attached to or entering the distal end of the introducer, the first and second proximal ends of the guide wire having different cross sectional geometries;
a probe capable of being extended over the guide wire from the distal end of the introducer; and
a proximal handle for externally causing the guide wire and probe to be extended from the distal end of the introducer and externally guiding the guide wire and probe within an intervertebral disc.

18. An intervertebral disc device according to claim 17 wherein the device further includes an introducer, the first proximal end of the guide wire being attached to the introducer adjacent a distal end of the introducer, the second proximal end of the guide wire being extendable from the introducer distal end to form the loop.

19. An intervertebral disc device according to claim 17 wherein the first and second proximal ends of the guide wire are each separately extendable from the introducer distal end to form the loop.

20. An intervertebral disc device according to claim 17 wherein the device further includes flexible tubing disposed between the proximal handle and the introducer.

21. An intervertebral disc device according to claim 17 wherein the different cross sectional geometries of the first and second proximal ends are selected such that the cross sectional geometry of the first proximal end is a compliment of the cross sectional geometry of the second proximal end.

22. An intervertebral disc device according to claim 21 wherein:
the first proximal end has a round cross section,
the second proximal end has a thin, concave cross section and a concave side, and
the first proximal end can be folded into the concave side.

23. An intervertebral disc device according to claim 17 wherein the probe further includes an electromagnetic energy device capable of supplying energy within the intervertebral disc.

24. An intervertebral disc device according to claim 23 wherein the electromagnetic energy device is capable of delivering energy selected from a group consisting of coherent light, incoherent light, RF waves, microwaves, and ultrasound waves.

25. An intervertebral disc device according to claim 23 wherein the electromagnetic energy device comprises electrodes adapted to deliver RF energy.

26. An intervertebral disc device according to claim 25 wherein the RF electrodes have a monopolar configuration.

27. An intervertebral disc device according to claim 25 wherein the RF electrodes have a bipolar configuration.

28. An intervertebral disc device according to claim 23 wherein the electromagnetic energy device comprises a resistive heating mechanism.

29. An intervertebral disc device according to claim 17 wherein the handle further comprises a guide wire control element for controlling the movement of the guide wire adjacent a distal end of the device.

30. An intervertebral disc device according to claim 17 wherein the probe further includes a functional element which performs a function selected from the group consisting of transmitting energy to tissue within an intervertebral disc, delivering material to within an intervertebral disc, and removing material within an intervertebral disc.

31. An intervertebral disc device according to claim 16 wherein the first proximal end has a round cross section and the second proximal end has a thin, concave cross section and a concave side.

32. An intervertebral disc device comprising:
a probe capable of being extended from a distal end of an introducer that is percutaneously delivered into an interior of an intervertebral disc, the probe forming a loop when extended from the distal end of the introducer, the loop having first and second proximal ends external to the introducer which are brought together adjacent the introducer distal end to form the loop by the proximal ends being either attached to or entering the distal end of the introducer; and
a proximal handle for externally causing the probe to be extended from the distal end of the introducer and externally guiding the probe within an intervertebral disc, the handle including a probe control element for controlling the movement of the probe adjacent a distal end of the device.

33. An intervertebral disc device comprising:
a guide wire capable of being extended from a distal end of an introducer that is percutaneously delivered into an interior of an intervertebral disc, the guide wire forming a loop when extended from the distal end of the introducer, the loop having first and second proximal ends external to the introducer which are brought together adjacent the introducer distal end to form the loop by the proximal ends being either attached to or entering the distal end of the introducer;

a probe capable of being extended over the guide wire from the distal end of the introducer; and a proximal handle for externally causing the guide wire and probe to be extended from the distal end of the introducer and externally guiding the guide wire and probe within an intervertebral disc, the handle including a guide wire control element for controlling the movement of the guide wire adjacent a distal end of the device.

* * * * *